(12) United States Patent
Jinno

(10) Patent No.: US 7,043,338 B2
(45) Date of Patent: *May 9, 2006

(54) MANIPULATOR

(75) Inventor: Makoto Jinno, Ota-Ku (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/893,921

(22) Filed: Jul. 20, 2004

(65) Prior Publication Data

US 2004/0267406 A1    Dec. 30, 2004

Related U.S. Application Data

(62) Division of application No. 09/964,459, filed on Sep. 28, 2001.

(30) Foreign Application Priority Data

Sep. 29, 2000    (JP)    ............................. 2000-298365

(51) Int. Cl.
     *G06F 19/00*      (2006.01)

(52) U.S. Cl. ........................... 700/245; 600/130; 606/1; 901/28

(58) Field of Classification Search ................ 700/245, 700/247, 260, 258, 262, 263; 600/130, 595, 600/248; 606/1, 139; 74/490.01, 490.06; 901/28

See application file for complete search history.

(56) References Cited

U.S. PATENT DOCUMENTS 5,797,900 A    8/1998    Madhani et al.

(Continued)

FOREIGN PATENT DOCUMENTS

| JP | 8-173442 | 7/1996 |
|---|---|---|
| JP | 2000-350735 | 12/2000 |

OTHER PUBLICATIONS

Mack, Minimally invasive and robotic surgery, 2001, Internet, pp. 568-572.

(Continued)

*Primary Examiner*—Yonel Beaulieu
*Assistant Examiner*—McDieunel Marc
(74) *Attorney, Agent, or Firm*—Oblon, Spivak, McClelland, Maier & Neustadt, P.C.

(57) ABSTRACT

A manipulator comprises an operation command unit provided with an attitude adjusting unit and an end effector control unit, a connecting unit having one end connected to the operation command unit, a working unit connected to the other end of the connecting unit and provided with an end effector and a support unit supporting the end effector for motions, and a control unit that transmits an operation command provided by the attitude adjusting unit to the support unit to adjust the attitude of the end effector and transmits an operation command provided by the end effector control unit to the end effector to operate the end effector. The support unit includes a first joint capable of turning about a first axis perpendicular to the center axis of the connecting unit, and a second joint capable of turning about a second axis perpendicular to the first axis. The end effector can be turned for rolling about an axis substantially parallel to the second axis of the second joint. The attitude adjusting unit has a third joint having a third axis perpendicular to the center line of the connecting unit. The end effector control unit is formed such that the fingers of an operator gripping operating members included in the end effector control unit extend substantially in parallel to the fourth axis.

7 Claims, 21 Drawing Sheets

U.S. PATENT DOCUMENTS

| | | |
|---|---|---|
| 6,371,952 B1 | 4/2002 | Madhani et al. |
| 6,385,509 B1 | 5/2002 | Das et al. |
| 6,470,236 B1 | 10/2002 | Ohtsuki |
| 6,522,949 B1 | 2/2003 | Ikeda et al. |
| 6,587,750 B1 | 7/2003 | Gerbi et al. |
| 6,594,552 B1 | 7/2003 | Nowlin et al. |
| 6,889,116 B1 * | 5/2005 | Jinno .................. 700/245 |
| 2002/0040217 A1 * | 4/2002 | Jinno ...................... 606/1 |

OTHER PUBLICATIONS

Butner et al., A real-time system for tele-surgery, 2001, IEEE, pp. 236-243.

Lee et al., A novel method of surgical instruction: international telementoring, 1198, Internet, pp. 1-4.

Bate et al., The feasibility of force control over the internet, 2001, Internet, pp. 146-151.

* cited by examiner

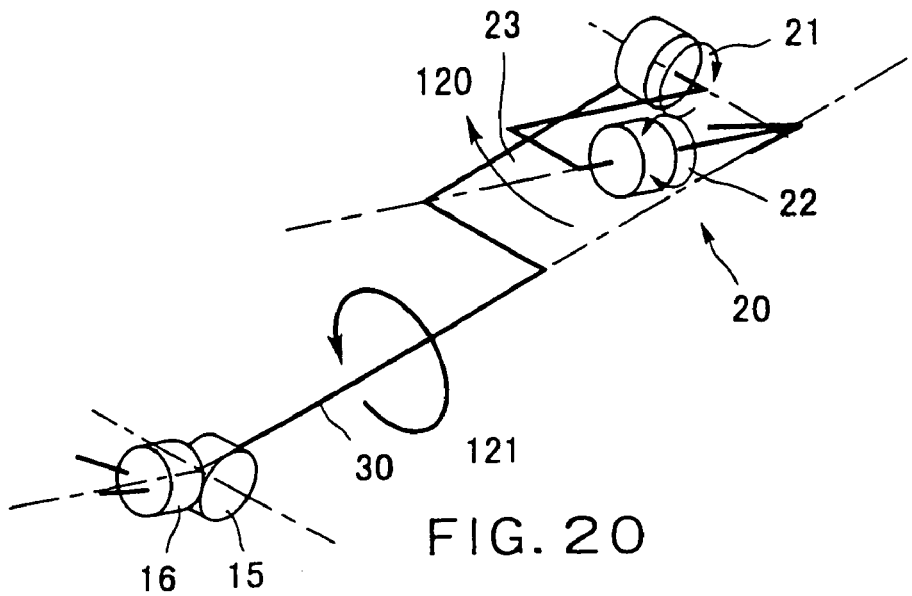
FIG. 20
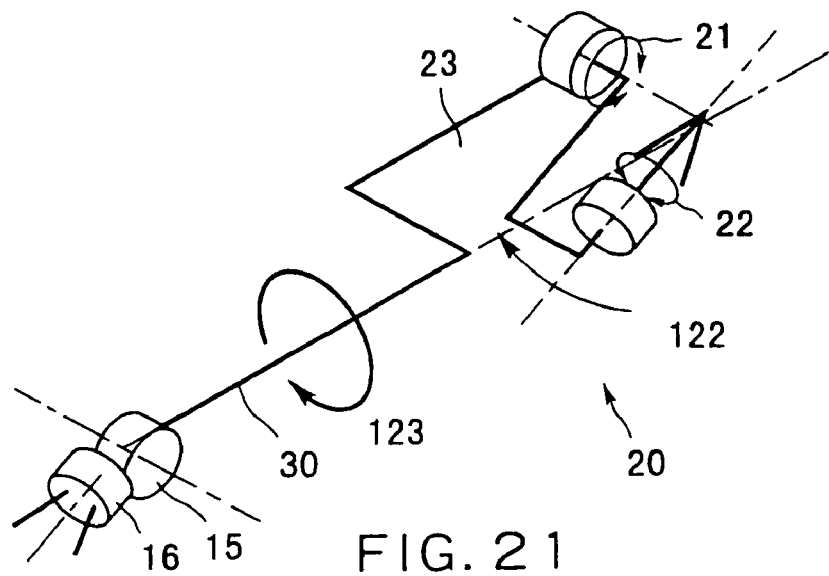
FIG. 21
| THIRD SHAFT | BENDING STRESS | TORQUE |
|---|---|---|
| + | + | + |
| + | − | − |
| − | + | − |
| − | − | + |
FIG. 22

MANIPULATOR

CROSS REFERENCE TO RELATED APPLICATION

This application is a division of and claims the benefit of priority under 35 USC §120 to U.S. application Ser. No. 09/964,459, filed Sep. 28, 2001, and is based upon and claims the benefit of priority under 35 USC §119 to Japanese Patent Application No. 2000-298365, filed Sep. 29, 2000, the entire contents which hare incorporated herein by reference.

BACKGROUND OF THE INVENTION

1. Field of the Invention

The present invention relates to a manipulator and, more particularly, to a medical manipulator of a simple mechanism excellent in operability.

2. Description of the Related Art

Referring to FIG. 25, when practicing laparoscopic surgical operation, such as cholecystectomy, some small holes 151, 152 and 153 are formed in the abdomen of a patient 150 and tubes 154 are inserted in the holes 151, 152 and 153. An endoscope 161 and forceps 171 and 172 are inserted through the tubes 154 in the abdomen. An operator 160, i.e., a surgeon, performs a surgical operation observing images taken by the endoscope 161 and displayed by a monitor 162. Such an operative method does not need laparotomy and reduces physical burden on the patient and reduces greatly the number of days necessary for the patient to recover and to leave the hospital after the operation. However, it is a problem in some cases that the operator 160 is unable to observe a diseased part directly. Furthermore, the forceps 171 and 172 are provided with only grippers capable of opening and closing, it is difficult to change the attitude of the grippers freely and hence the forceps 171 and 172 are poorly operable. Accordingly, only skilled operators are able to perform the foregoing operative method properly. It takes a very long time for operators to attain proficiency in the operative method using the endoscope.

Studies have been made to solve such problems by applying remote-controlled robots, such as master/slave manipulators, to the medical field. The remote-controlled robot is a robot system including a master arm to be operated by an operator, and a slave arm to act on a diseased part. The master arm and the slave arm are completely separated. Electric signals representing commands provided by operating the master arm are given to the slave arm. Usually the master arm and the slave arm are articulated arms having at least six degrees of freedom of motion. The master/slave manipulator is provided with controllers for controlling slave arms for operations in six degrees of freedom of motion and is a complicated system including many electric control systems, many parts and many wiring lines. Because of its complexity, the reliability of operations of the master/slave manipulator is not on a satisfactorily high level. The master/slave manipulator is a large-scale system, expensive and needs a high maintenance cost. The operator operates the master/slave manipulator at a position remote from the patient and hence the operator is unable to give medical treatment quickly to the patient in an emergency.

The inventors of the present invention proposed a medical manipulator shown in FIG. 26 in Jpn. Pat. App. No. Hei 11-165961. As shown in FIG. 26, this previously proposed medical manipulator includes an operation command unit 20 including a attitude adjusting unit 23 and an end effector control unit 24, a connecting unit 30 having one end connected to the operation command unit 20, a working unit 10 connected to the other end of the connecting unit 30 and provided with an end effector 14 and support units 15 and 16 supporting the end effector 14 for operations in at least two degrees of freedom of motion, and a controller, not shown, capable of transmitting an operation command provided by the attitude adjusting unit 23 to the support units 15 and 16 to adjust the attitude of the end effector 14 and of transmitting an operation command provided by the end effector control unit 24 to the end effector 14 to operate the end effector 14. In the working unit 10 and the operation command unit 20, the support units 15 and 16 have a pitching shaft and a yawing shaft, respectively, and the end effector 14 is a gripper.

Referring to FIG. 27, when the medical manipulator is used for suture, the end effector 14 grips a curved suture needle 180 threaded with a thread 181, sticks the suture needle 180 into a part to be sutured and moves the curved suture needle 180 along a circular path. Since required operations and the degree of freedom of motion are not properly coordinated in the known medical manipulator shown in FIG. 26, the operation command unit 20 is unable to operate smoothly for operations in directions intended by the operator. Thus, the operability of the known medical manipulator is unsatisfactory. When the working unit 10 and the operation command unit 20 are in some positions, respectively, the degree of freedom of motion of the end effector 14 is reduced, the end effector 14 is set in a singular attitude and the operability of the end effector 14 in particular directions becomes unsatisfactory. Moreover the gripping force of the end effector 14 is insufficient.

SUMMARY OF THE INVENTION

The present invention has been made in view of the aforesaid problems in the conventional medical manipulators and it is therefore an object of the present invention to provide a manipulator having simple construction and high reliability and excellent in operability.

According to one aspect of the present invention, a manipulator includes an operation command unit provided with a attitude adjusting unit and an end effector control unit, a connecting unit having one end connected to the operation command unit, a working unit connected to the other end of the connecting unit and provided with an end effector and a support unit supporting the end effector for motions in at least two degrees of freedom of motion, and a control unit that transmits an operation command provided by the attitude adjusting unit to the support unit to adjust the attitude of the end effector and transmits an operation command provided by the end effector control unit to the end effector to operate the end effector; wherein the support unit includes a first joint capable of turning about a first axis perpendicular to the center axis of the connecting unit, and a second joint capable of turning about a second axis perpendicular to the first axis, the end effector has a center axis substantially parallel to the second axis, the attitude adjusting unit includes a third joint capable of turning about a third axis perpendicular to the center axis of the connecting unit and a fourth joint capable of turning about a fourth axis perpendicular to the third axis, the end effector control unit is provided to be gripped by fingers extending substantially in parallel to the fourth axis.

In the manipulator according to the present invention, the end effector has two working joints mounted on the second joint, the two working joints being capable of turning about the second axis, the two working joints are rotated in the same direction to rotate the second joint, and the two working joints are rotated in opposite directions, respectively, to drive the end effector for gripping and releasing actions.

In the manipulator according to the present invention, two working links are supported on the two working joints, respectively, and capable of turning about axes in directions parallel to and in directions perpendicular to the axis of the two working joints, and the working links are rotatably joined together.

The manipulator according to the present invention may further include a sensor capable of measuring force acting in a direction perpendicular to the axes of the third and fourth joint and included in the operation command unit; and an actuator combined with the connecting unit and capable of applying a torque to the connecting unit to urge the connecting unit to turn about its axis; wherein the actuator is controlled on the basis of a value measured by the sensor.

In the manipulator according to the present invention, the sign of the torque produced by the actuator may be controlled on the basis of the relation between the sign of an angle indicating the angular position of the third joint and that of the value measured by the sensor.

In the manipulator according to the present invention, the torque produced by the actuator may be controlled to vary in proportion to the value measured by the sensor.

In the manipulator according to the present invention, a working unit provided with an end effector and a support unit supporting the end effector for motions in at least two degrees of freedom of motion; wherein the support unit includes a first joint capable of turning about a first axis, and a second joint capable of turning about a second axis perpendicular to the first axis, wherein the working unit has two working joints mounted on the second joint, the two working joints being capable of turning about the second axis,the two working joints are rotated in the same direction to rotate the second joint, and the two working joints are rotated in opposite directions, respectively, to drive the end effector for gripping and releasing actions.

In the manipulator according to the present invention, two working links are supported on the two working joints, respectively, and capable of turning about axes in directions parallel to and in directions perpendicular to the axes of the two working joints, and the working links are rotatably joined together.

According to the present invention, the support unit is capable of supporting the end effector for motions in at least two degrees of freedom of motion, and the operation command unit and the working unit are connected mechanically by the connecting unit. Therefore, satisfactory operability and high reliability, which are the features of the manipulator previously proposed in Jpn. Pat. App. No. Hei 11-165961, are not spoiled. Since the actual actions of the operator, such as operator's actions for moving a curved suture needle for suturing, and the motions of the manipulator are identical, the operation command unit can be smoothly moved in a direction desired by the operator. Thus, the manipulator is excellent in operability. Since operating force exerted by the operator is assisted by power when the end effector is set in a singular attitude or an attitude similar to the particular attitude, the operability of the end effector in particular directions does not becomes quite unsatisfactory and the end effector is able to exert a sufficiently high gripping force.

BRIEF DESCRIPTION OF THE DRAWINGS

The above and other objects, features and advantages of the present invention will become more apparent from the following description taken in connection with the accompanying drawings, in which:

FIG. 20 is a skeleton drawing of assistance in explaining a method of controlling the medical manipulator in the second embodiment;

FIG. 21 is a skeleton drawing of assistance in explaining a method of controlling the medical manipulator in the second embodiment;

FIG. 22 is a table of assistance in explaining a method of controlling the medical manipulator in the second embodiment;

DESCRIPTION OF THE PREFERRED EMBODIMENTS

Figure 1:
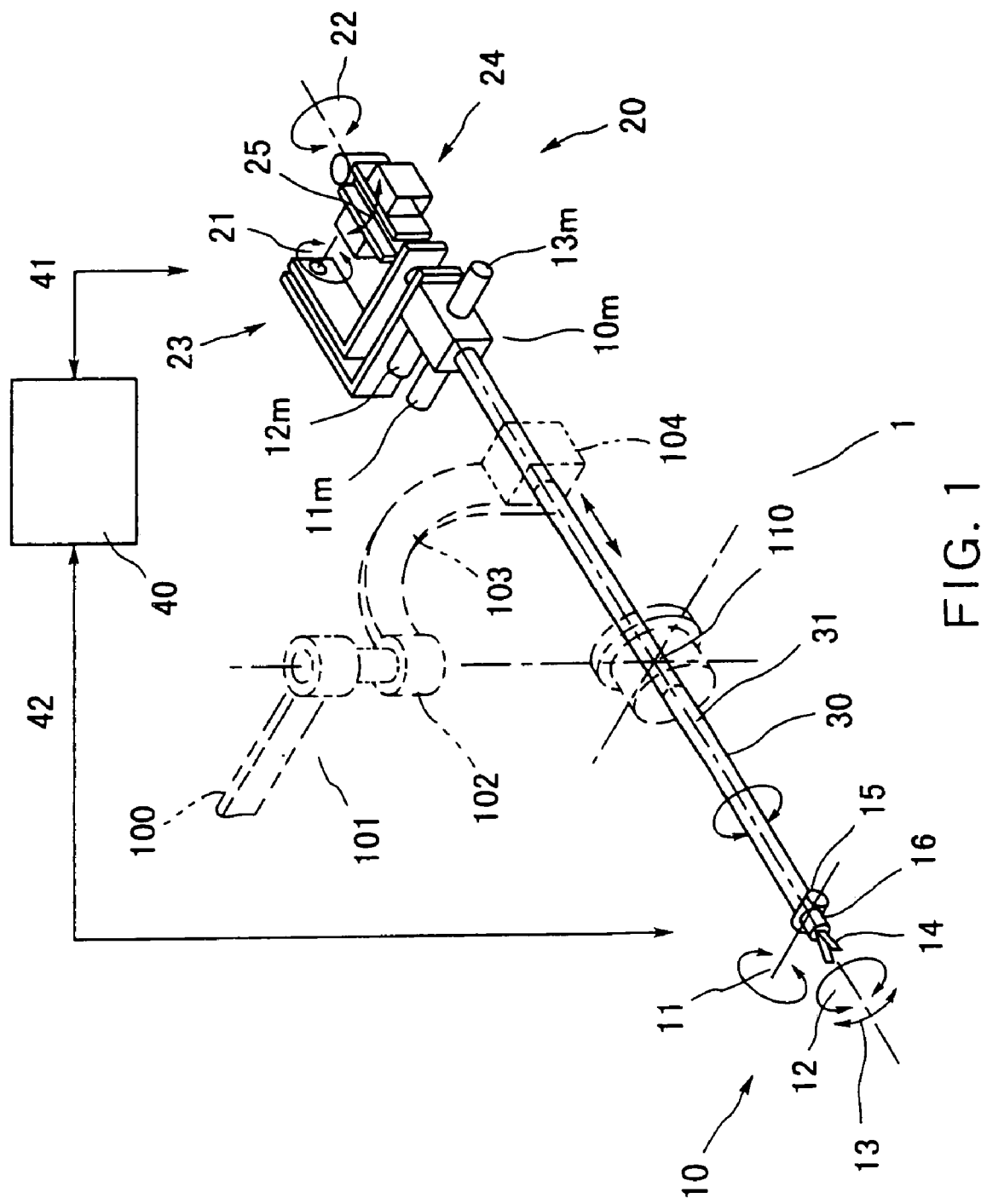
FIG. 1 is a schematic perspective view of a medical manipulator in a first embodiment according to the present invention.
Figure 2:
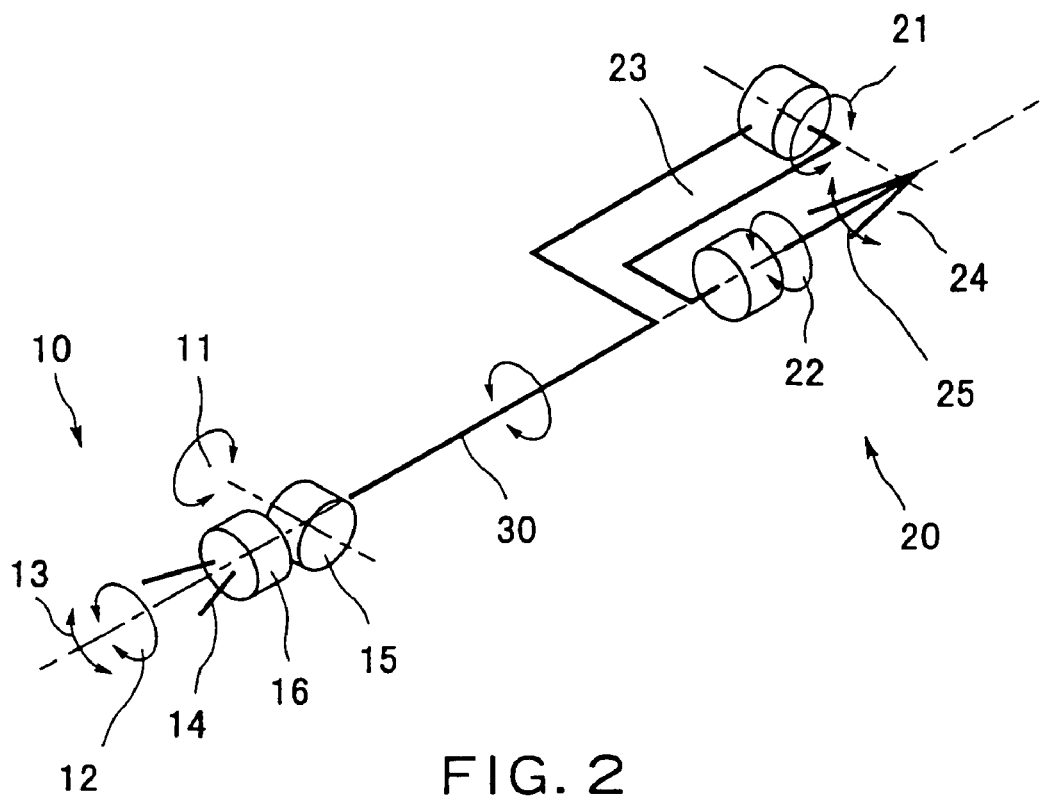
FIG. 2 is a skeleton drawing of the medical manipulator shown in FIG. 1.
Figure 3:
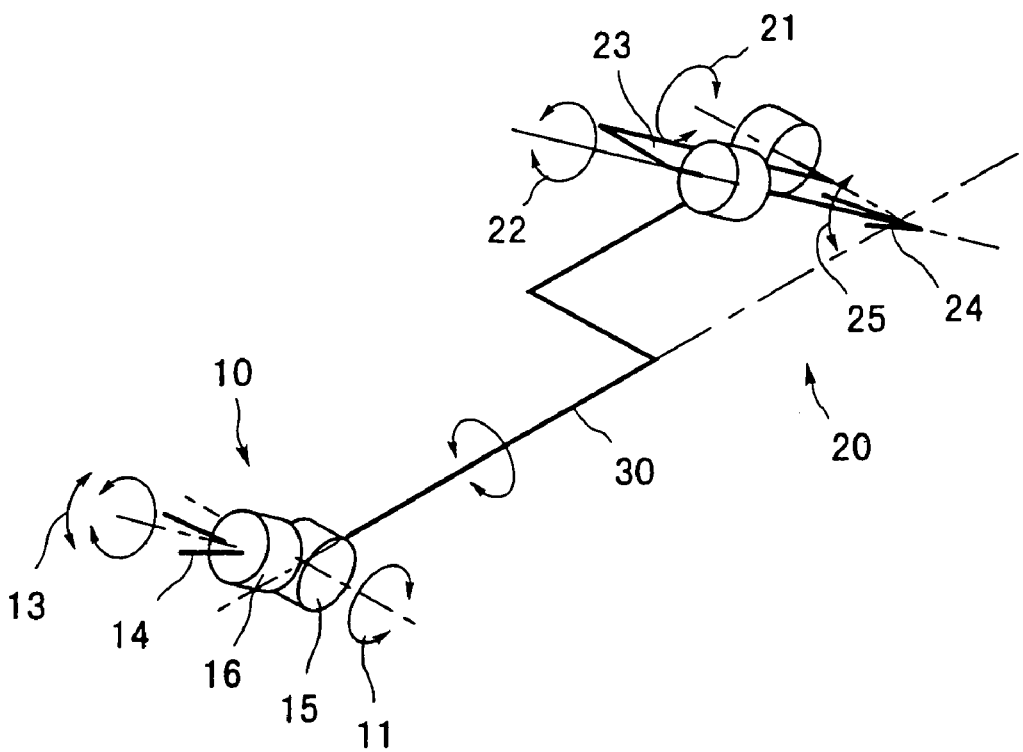
FIG. 3 is a skeleton drawing of assistance in explaining the operation of the medical manipulator shown in FIG. 1.

FIG. 1 is a schematic perspective view of a medical manipulator 1 in a first embodiment according to the present invention, and FIGS. 2 and 3 are skeleton drawings of the medical manipulator 1 shown in FIG. 1 of assistance in explaining the degree of freedom of motion and operations of the medical manipulator 1.

Referring to FIGS. 1 and 2, the medical manipulator 1 has a working unit 10, an operation command unit 20, and a connecting unit 30 having opposite ends connected to the working unit 10 and the operation command unit 20.

The working unit 10 has a support unit and an end effector. The support unit includes a first joint 11 having a first rotation axis perpendicular to the center axis 31 of the connecting unit 30 and a second joint 12 having a second rotation axis perpendicular to the first rotation axis of the first joint 11. A gripper 14 included in the end effector and capable of performing gripping/releasing actions 13 has a center axis substantially parallel to the second rotation axis of the second joint 12. The working unit 10 has a pitching-axis joint 15 and a rolling-axis joint 16 supporting the gripper 14 for motions in two degrees of freedom of motion.

The operation command unit 20 has attitude adjusting unit 23 including a third joint 21 having a third rotation axis perpendicular to the center axis 31 of the connecting unit 30 and a fourth joint 22 having a fourth rotation axis perpendicular to the third rotation axis of the third joint 21, and an end effector control unit 24. The end effector control unit 24 is formed such that directions 201a and 202a (FIG. 28) in which the fingers of an operator grasping the end effector control unit 24 extend are substantially parallel to the fourth axis 22a of the fourth joint 22. The gripping/releasing action 13 of the gripper 14 is caused by a control action indicated by the arrow 25 (herein after referred to as "control action 25") of the end effector control unit 24, which will be described in detail later with reference to FIGS. 7 to 10 and 28.

In FIGS. 1 and 2, the center axis 31 of the connecting unit 30, the first axis of the first joint 11 and the second axis of the second joint 12 intersect each other at a single point, and the center axis 31 of the connecting unit 30, the third axis of the third joint 21 and the fourth axis of the fourth joint 22 intersect each other at a single point. Although those axes do not necessarily intersect each other at a single point, the gripper 14 revolves along a circular path of an excessively great radius if the offset of the gripper 14 is excessively great. If the offset of the attitude adjusting unit 23 is great, a torque that cause attitude adjustment acts on the attitude adjusting unit 23 when position adjustment is necessary.

Angle sensors, such as encoders or potentiometers, are incorporated into the operation command unit 20 to measure angles of turning of the third joint 21 and the fourth joint 22. An action sensor, such as an angle sensor or a switch, is incorporated into the end effector control unit 24 to measure control actions performed by the operator to operate the end effector 14. The sensors sends signals representing commands 41 provided by the attitude control unit 20 to a controller 40. The controller 40 executes predetermined calculations on the basis of the input commands 41 to drive and control the first joint 11, the second joint 12 and the gripper 14.

The gripper 14 can be directly operated for position adjustment because the connecting unit 30 connects the working unit 10 and the operation command unit 20. The connecting unit 30 as a rolling shaft, the first joint 11 as a pitching shaft and the second joint 12 as a rolling shaft enable the gripper 14 to move for motions in three degrees of freedom of motion and hence the gripper 14 can be set in an optional attitude. The connecting unit 30 as a rolling shaft, the third joint 21 as a pitching shaft and the fourth joint 22 as a rolling shaft enable the end effector control unit 24 to move for motions in three degrees of freedom of motion and hence the end effector control unit 24 can be set in an optional attitude. The use of the connecting unit 30 as a common rolling shaft reduces the cost of the medical manipulator 1. An ordinary manipulator has a problem relating to calculation and a problem that a specific shaft moves extraordinarily rapidly when the gripper 14 is set in a singular attitude. Since the working unit 10 and the end effector control unit 20 of the medical manipulator 1 of the present invention have the same construction, the medical manipulator 1 of the present invention is free from such problems.

A driving unit 10m including, for example, motors and reduction gears for driving the first joint 11 and the second joint 12 for turning and driving the gripper 14 for the gripping/releasing actions 13 is disposed at a position on the connecting unit 30 near the operation command unit 20. The first joint 11 and the second joint 12 of the working unit 10 are turned and the gripper 14 of the working unit 10 is driven for the gripping/releasing actins by the driving power of driving devices 11m, 12m and 13m included in the driving unit 10m.

An articulated mechanism including the first joint 11 and the second joint 12 of support unit of the working unit 10 and an articulated mechanism including the third joint 21 and the fourth joint 22 of the attitude adjusting unit 23 are identical. Therefore, the first joint 11 turns through an angle by which the third joint 21 is turned, and the second joint 12 turns through an angle by which the fourth joint 22 is turned. For example, when the operator turns the third joint 21 for attitude adjustment as shown in FIG. 3, the first joint 11 of the working unit 10 turns accordingly.

Figure 27:
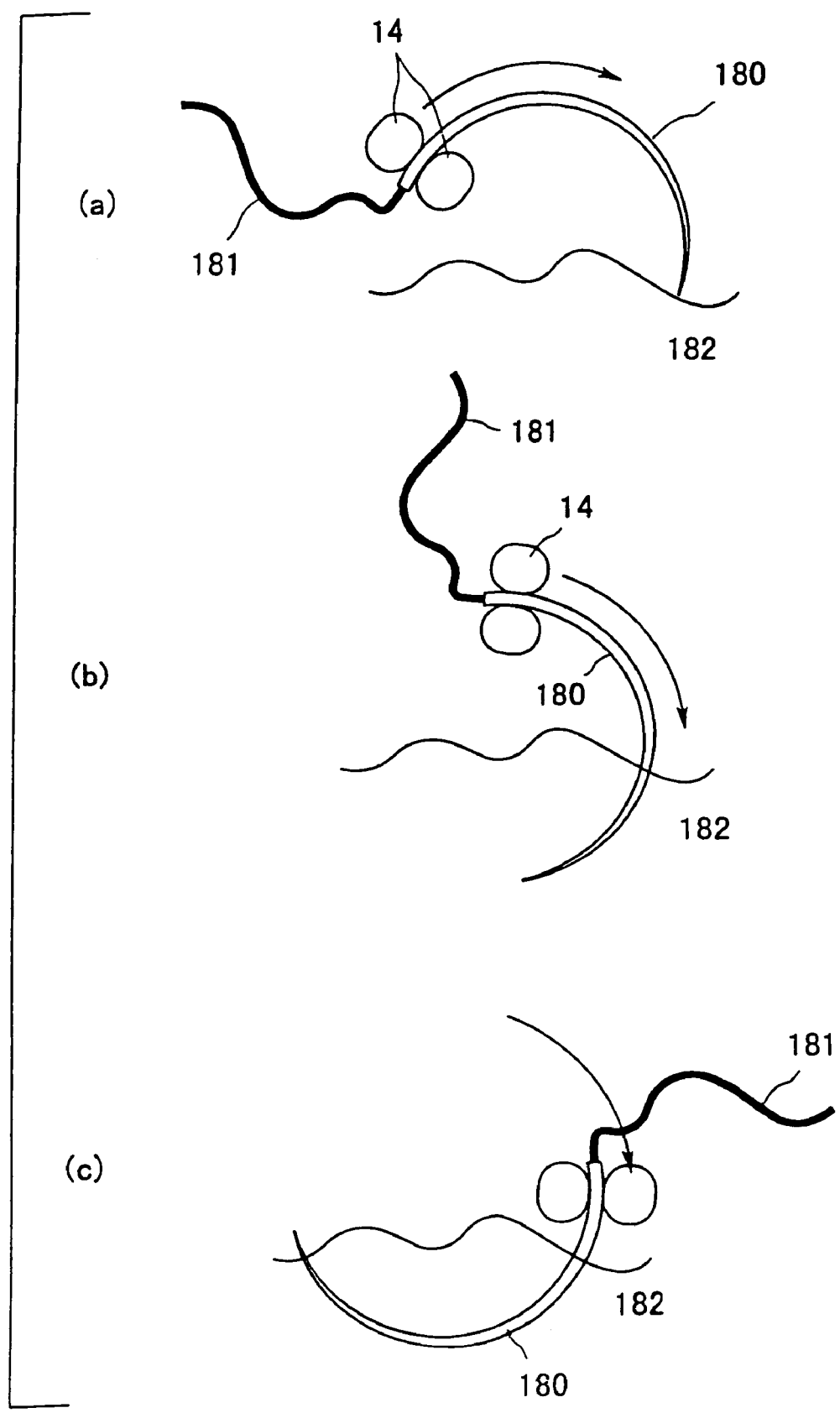
FIGS. 27(a), 27(b) and 27(c) are diagrammatic views of assistance in explaining a suturing operation.

Since the degrees of freedom of motion of the working unit 10 and the operation command unit 20 of the medical manipulator are designed such that the gripper 14 moves in the same direction as that in which the operator moves the operation command unit 20 for manipulating, for example, a curved needle for suture as shown in FIG. 27. For example, when the medical manipulator 1 is used for suture, the operator operates the operation command unit 20 to move the end effector 14 griping a curved suture needle so that the curved needle is stuck into a part to be sutured and the curved suture needle moves along a circular path. The circular movement of the curved needle coincides substantially with the turning motion of the fourth joint 22, and the third joint 21 and the connecting unit 30 do not need to be turned through large angles. Thus, the curved needle can be easily manipulated. The conventional manipulator carries out the same operations for manipulating the curved needle by combined motions of the motions in two degrees of freedom of motion of the end effector and the turning motion of the connecting unit. Thus, it is very difficult to manipulate the curved needle by the conventional manipulator for movement along the circular path intended by the operator.

Any support structure is unnecessary if the medical manipulator 1 is very lightweight. If the medical manipulator 1 is so heavy that the operator has difficulty in supporting the medical manipulator 1 for a long time or if the medical manipulator 1 needs a holding brake mechanism and a weight compensating mechanism for compensating its own weight, the medical manipulator 1 may be supported on a support mechanism 100 as indicated by broken lines in FIG. 1. The medical manipulator 1 is supported for turning motions about two axes on a virtual rotation center 110 (fixed point) and for uniaxial linear motions (motions in a polar coordinate system). For example, the support mechanism 100 includes a base, a position adjusting mechanism 101 capable of vertically moving relative to the base, a rotary unit 102 supported on a lower part of the position adjusting mechanism 101 so as to be turnable in a horizontal plane about a vertical axis, and a circular arm 103 having one end connected to the outer circumference of the rotary unit 102. The turning axis of the rotary unit 102 intersects the virtual rotation center 110 on the center axis 31 of the connecting unit 30. A connecting member 104 connects the other end of the circular arm 103 to the connecting unit 30. The connecting member 104 is able to move along a circular path on the circular arm 103. The connecting unit 30 is extended through the connecting member 104 so as to be linearly movable along the center axis 31.

Figure 4:
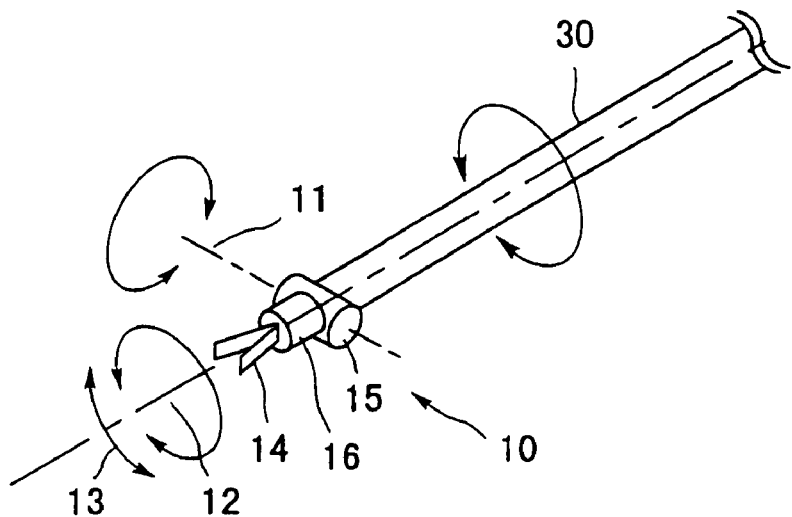
FIG. 4 is a schematic perspective view of a working unit included in the medical manipulator shown in FIG. 1.
Figure 5:
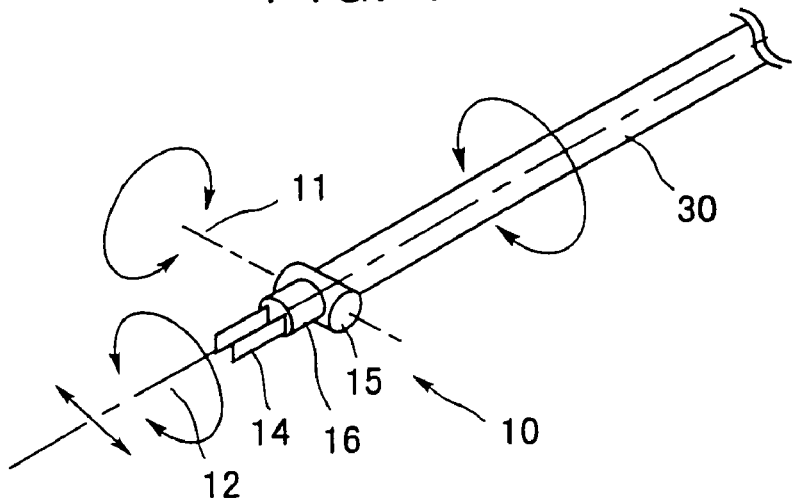
FIG. 5 is a schematic perspective view of a working unit included in the medical manipulator shown in FIG. 1.
Figure 6:
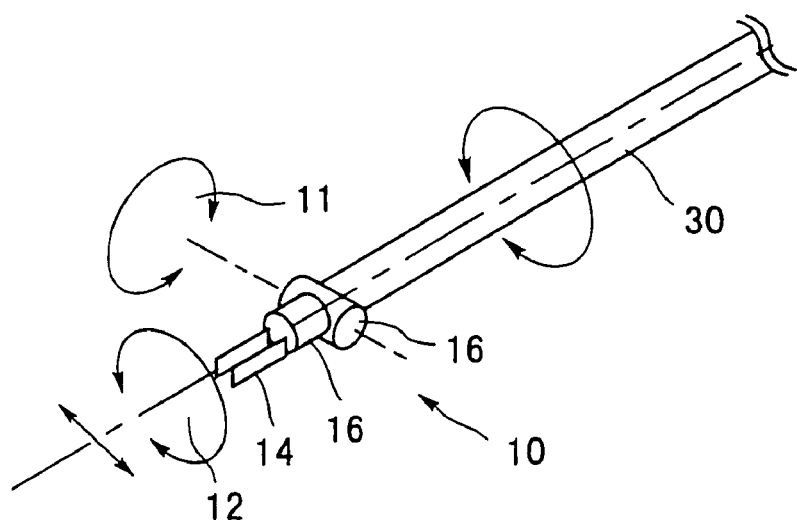
FIG. 6 is a schematic perspective view of a working unit included in the medical manipulator shown in FIG. 1.

FIGS. 4 to 6 show grippers 14 that can be applied to the end effector of the working unit 10 of the medical manipulator 1 in the first embodiment. FIG. 4 shows a gripper 14 having griping members capable of being moved like scissors blades for gripping/releasing actions 13, FIG. 5 shows a gripper 14 having gripping members capable of being moved toward and away from each other for gripping/releasing and FIG. 6 shows a gripper 14 dislocated with respect to the axis of the second joint 12. The gripper 14 may be set in any suitable disposition other than those shown in FIGS. 4 to 6, provided that the center axis thereof is substantially parallel to the axis of the second joint 12.

FIGS. 7 to 10 show the mechanisms of operation command units 20, particularly, end effector control units 24 which may be employed in the medical manipulator 1 in the first embodiment.

Figure 7:
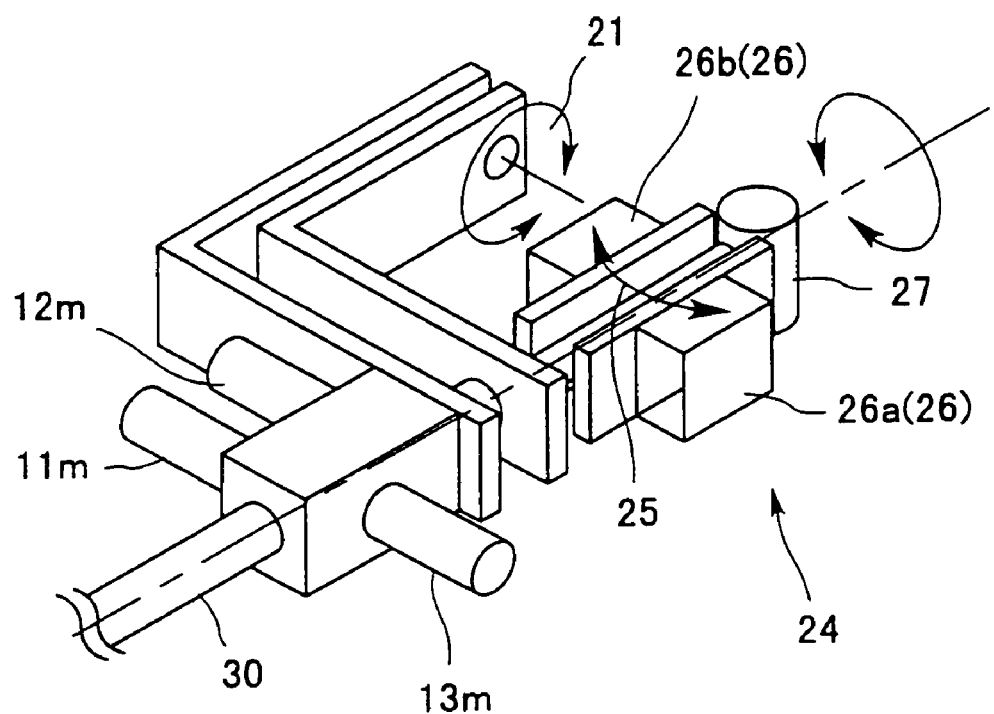
FIG. 7 is a schematic perspective view of an end effector control unit that may be employed in the medical manipulator shown in FIG. 1.

The end effector control unit 24 shown in FIG. 7 provides commands for operating the gripper 14 for gripping/releasing actions when a finger-operated control unit 26 is operated for gripping/releasing actions 25. The finger-operated control unit 26 is provided with two finger holders 26a and 26b for receiving the operator's thumb, and the operator's index and middle fingers, respectively. At least either the finger holder 26a or the finger holder 26b is supported pivotally on a support member 27 so that the distance between the finger holders 26a and 26b can be optionally changed. When the distance between the finger holders 26a and 26b is changed, the distance between the gripping bars of the gripper 14 changes accordingly. The angle between the finger holders 26a and 26b may be measured and the angle between the gripping bars of the gripper 14 may be adjusted according to the angle between the finger holders 26a and 26b. The gripping and the releasing positions of the finger holders 26a and 26b may be detected and the gripping bars of the gripper 14 may be set at gripping positions or releasing positions.

Figure 8:
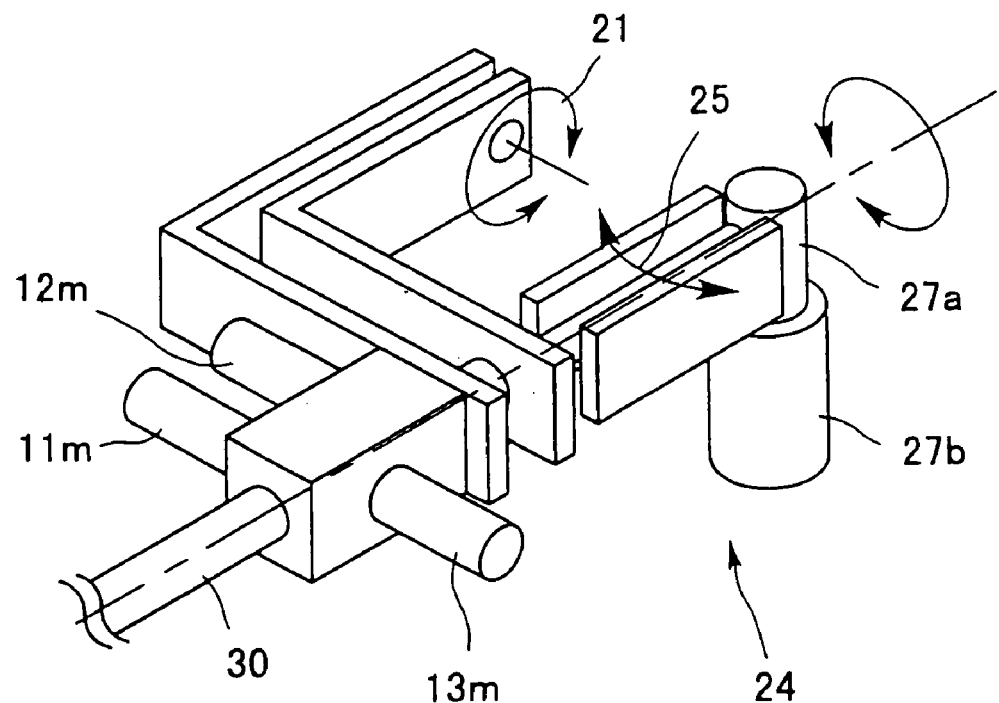
FIG. 8 is a schematic perspective view of an end effector control unit that may be employed in the medical manipulator shown in FIG. 1.

The end effector control unit 24 shown in FIG. 8 is provided with a support member 27 having a handle part 27b. The operator grips the handle part 27b with the middle or the little finger to operate the end effector control unit stably. The end effector control unit 24 may be provided with the finger-operated control unit 26, a resilient means capable of exerting a resilient releasing force or a locking mechanism for locking the end effector control unit 24 in a gripping state.

Figure 9:
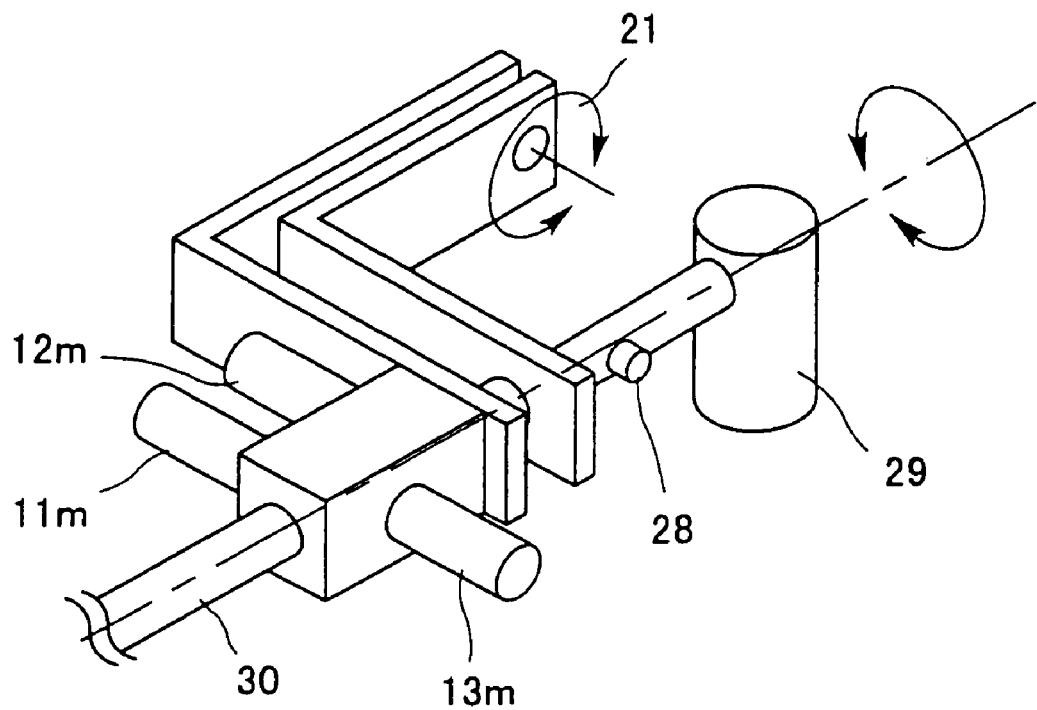
FIG. 9 is a schematic perspective view of an end effector control unit that may be employed in the medical manipulator shown in FIG. 1.
Figure 10:
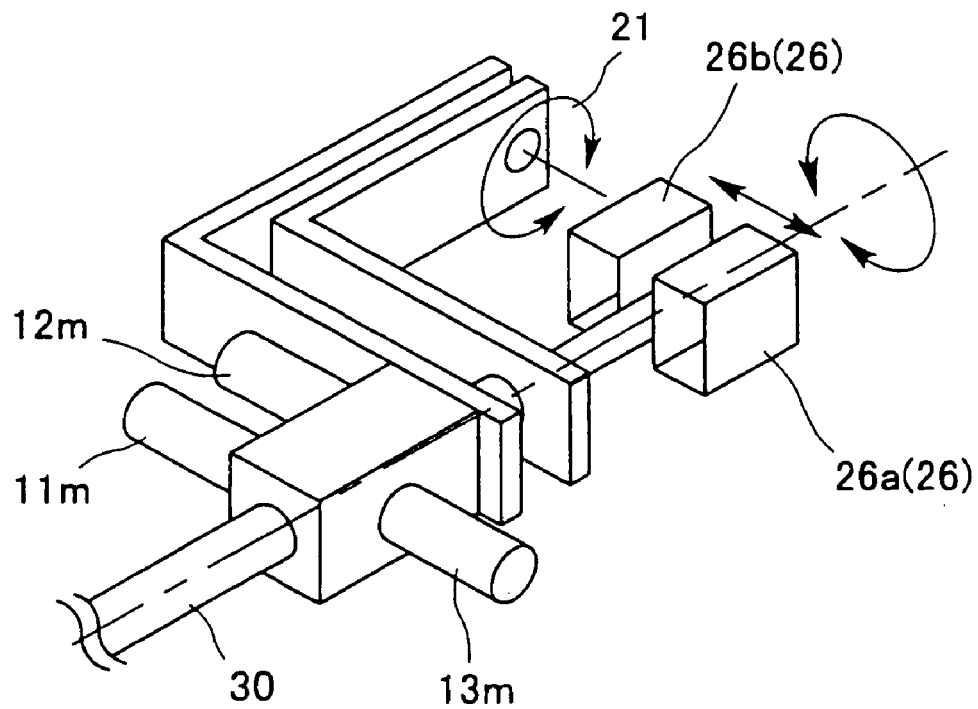
FIG. 10 is a schematic perspective view of an end effector control unit that may be employed in the medical manipulator shown in FIG. 1.

The end effector control unit 24 shown in FIG. 9 is provided with a handle 29 and a switch 28 disposed near the handle 29. The operator grips the handle 29 and operates the switch 28 to provide commands to drive the gripper 14 for the gripping/releasing actions 13. If the gripper 14 needs to be driven only for gripping and releasing, the simple end effector control unit 24 shown in FIG. 9 can be employed The end effector control unit 24 shown in FIG. 10 is provided with parallel finger holders 26a and 26b capable of being moved toward and away from each other.

Figure 28:
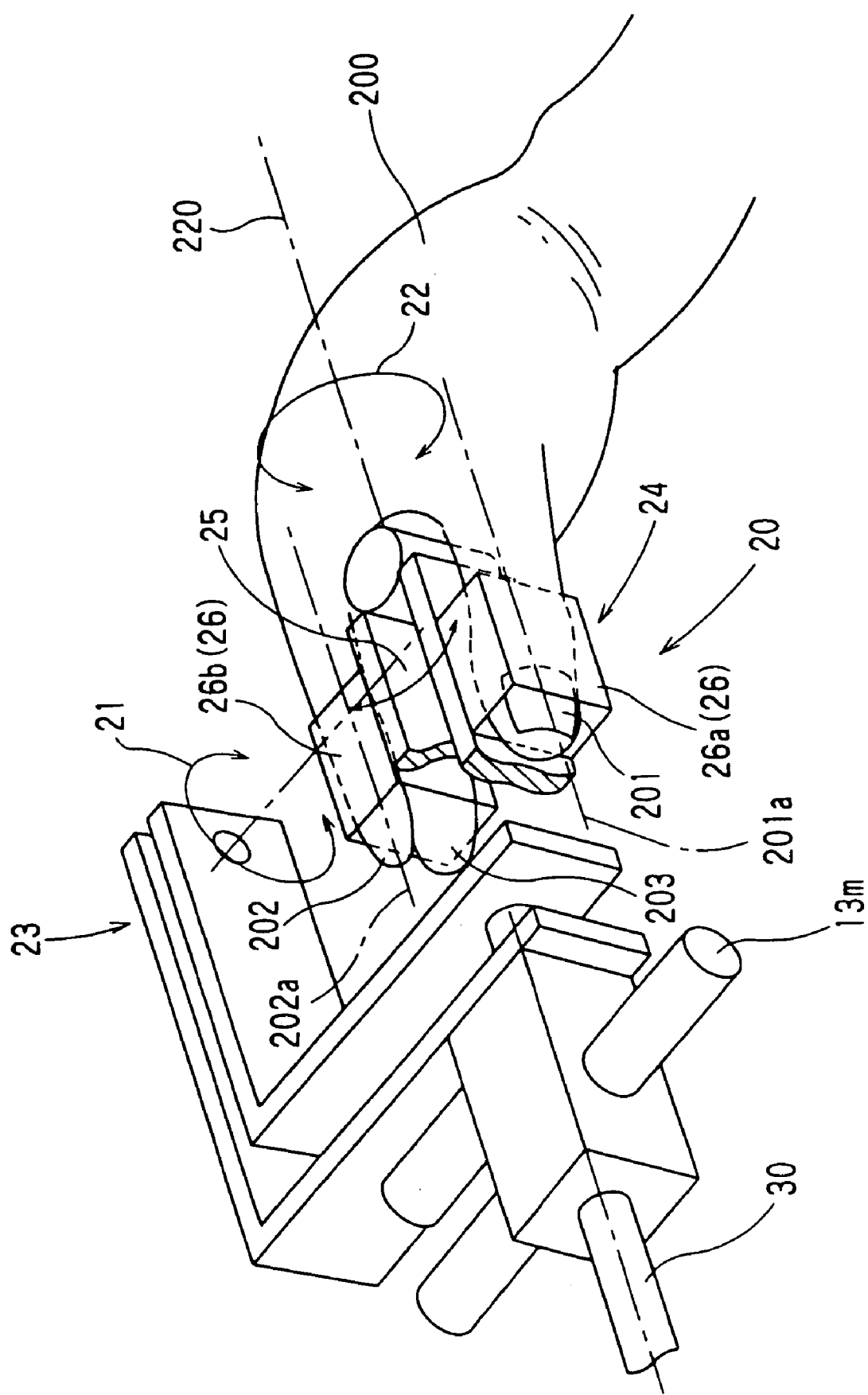
FIG. 28 is a perspective view of assistance in explaining the relation between the direction of operator's fingers holding an end effector control unit and the direction of the axis of a fourth joint.

FIG. 28 is a perspective view of assistance in explaining the operation of the end effector control unit 24 shown in FIG. 1 by the operator's hand 200. The operator's thumb 201 is inserted in a finger holder 26a, and the operator's forefinger 202 and/or middle finger 203 are inserted in a finger holder 26b. When the thumb 201, the forefinger 202 and/or the middle finger 203 are thus inserted in the finger holders 26a and 26b of the end effector control unit 24, the longitudinal axis 201a of the thumb 201, the longitudinal axis 202a of the forefinger 202 and the longitudinal axis 203a of the middle finger 203 are substantially parallel to the axis 22a of the fourth joint 22 as shown in FIG. 28. The same is true of the end effector control units 24 shown in FIGS. 7 to 10.

FIGS. 11 to 16 show working units 10 that may be employed in the medical manipulator 1 in the first embodiment. Grippers 14 are in a releasing state in FIGS. 11, 13 and 15, and grippers are in a gripping state in FIGS. 12, 14 and 16.

Figure 11:
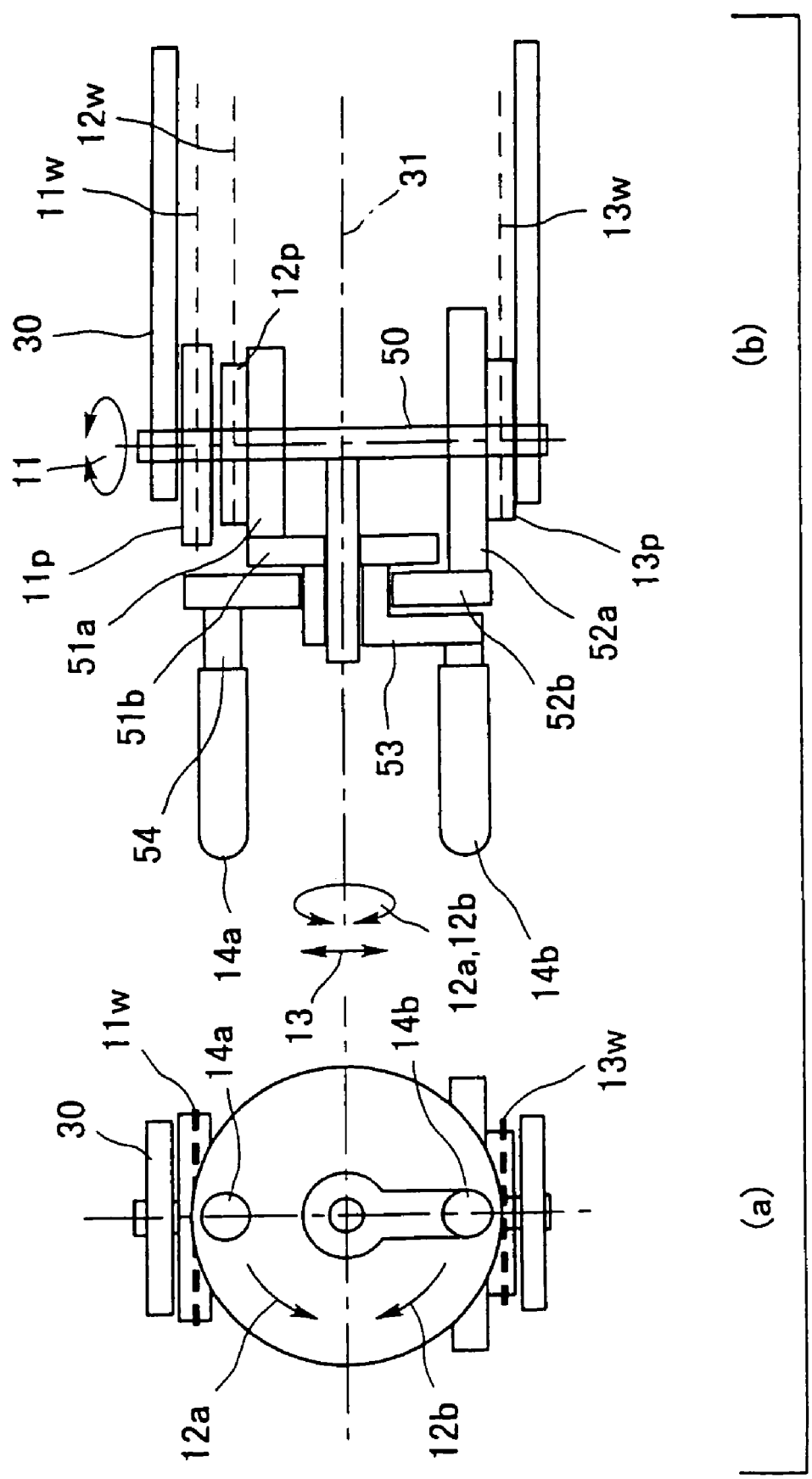
FIGS. 11(a) and 11(b) are a front elevation and a side elevation, respectively, of a working unit that may be employed in the medical manipulator shown in FIG. 1, in which gripping bars are at releasing positions, respectively.
Figure 12:
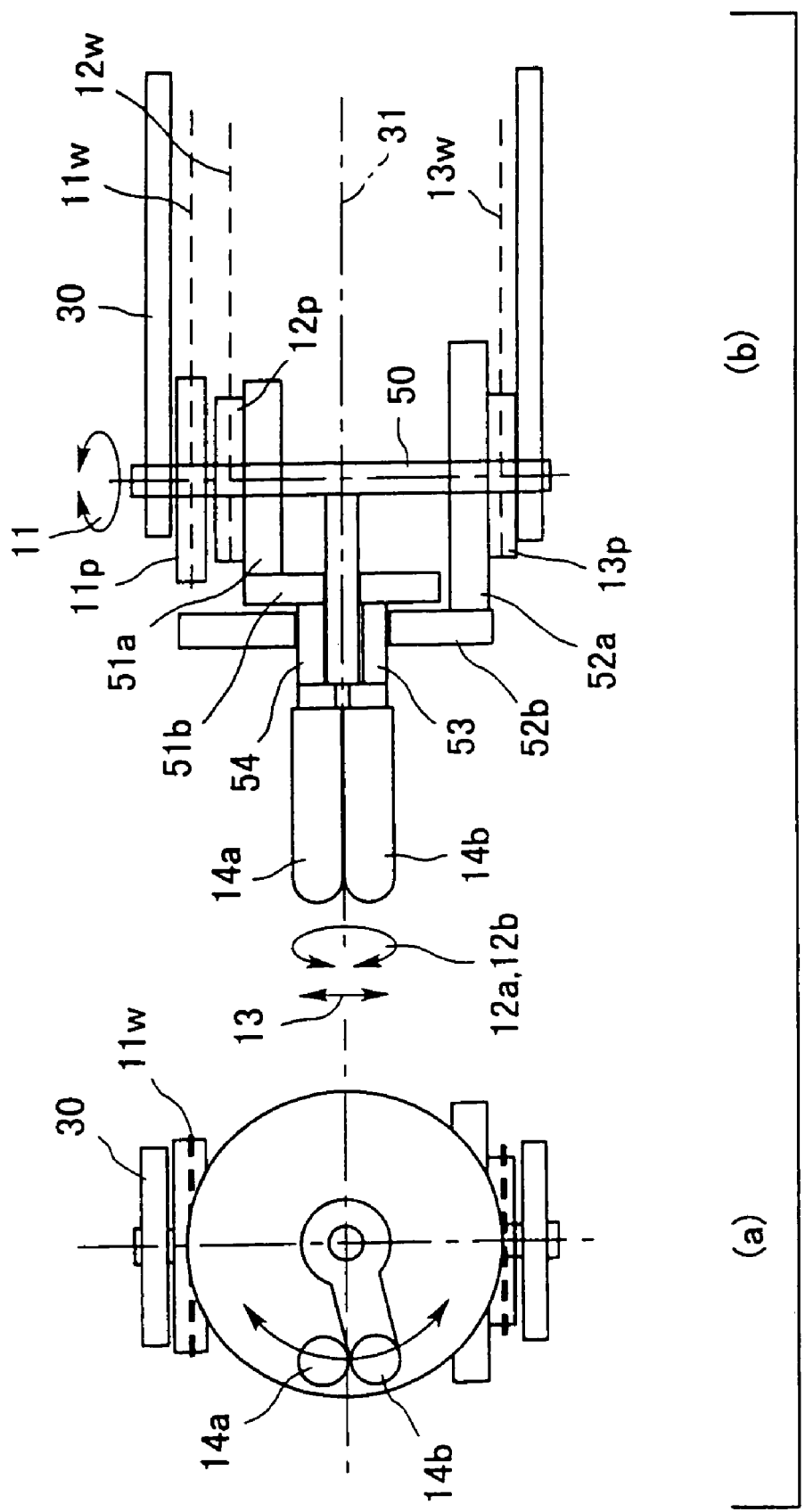
FIGS. 12(a) and 12(b) are a front elevation and a side elevation, respectively, of the working unit shown in FIG. 11 in a gripping state.

The working unit 10 shown in FIGS. 11 and 12 will be described. A rotating member 50 is supported for rotation relative to the connecting unit 30 on the first joint 11. A pulley 11p is mounted on the rotating member 50. The driving force of the driving device 11m (FIG. 1) is transmitted to the pulley 11p by a wire 11w to rotate the pulley 11p together with the first joint 11. Pulleys 12p and 13p are supported on the rotating member 50 for rotation relative to the rotating member 50. Bevel gears (or face gears). 51a and 52a are fixedly combined with the pulleys 12p and 13p, respectively. The bevel gears 51a and 52a are engaged with bevel gears 51b and 52b, respectively. The driving forces of the driving devices 12m and 13m (FIG. 1) are transmitted to the pulleys 12p and 13p by wires 12w and 13w, respectively. Consequently, the bevel gears 51b and 52b are rotated. The bevel gears 51b and 52b are supported on the second joint 12 for rotation about an axis perpendicular to the axis of the first joint 11 supporting the rotating member 50. Two shafts 12a and 12b are mounted on the shaft 12. Gripping bars 14a and 14b are fixedly connected to the bevel gears 51b and 52b by connecting members 53 and 54, respectively, so that the center axes thereof are substantially parallel to the axis of the second joint 12. Thus the gripping bars 14a and 14b can be individually driven by the driving devices 12m and 13m, respectively. When the shafts 12a and 12b are rotated in the same direction, the gripper 14 can be turned for rolling. When the shafts 12a and 12b are rotated in opposite directions, respectively, the gripper 14 can be driven for gripping/releasing operations. The driving actins of the driving devices 12m and 13m can be easily determined taking into consideration power transmitting methods by which the driving forces of the driving device 12m and 13m are transmitted.

Figure 13:
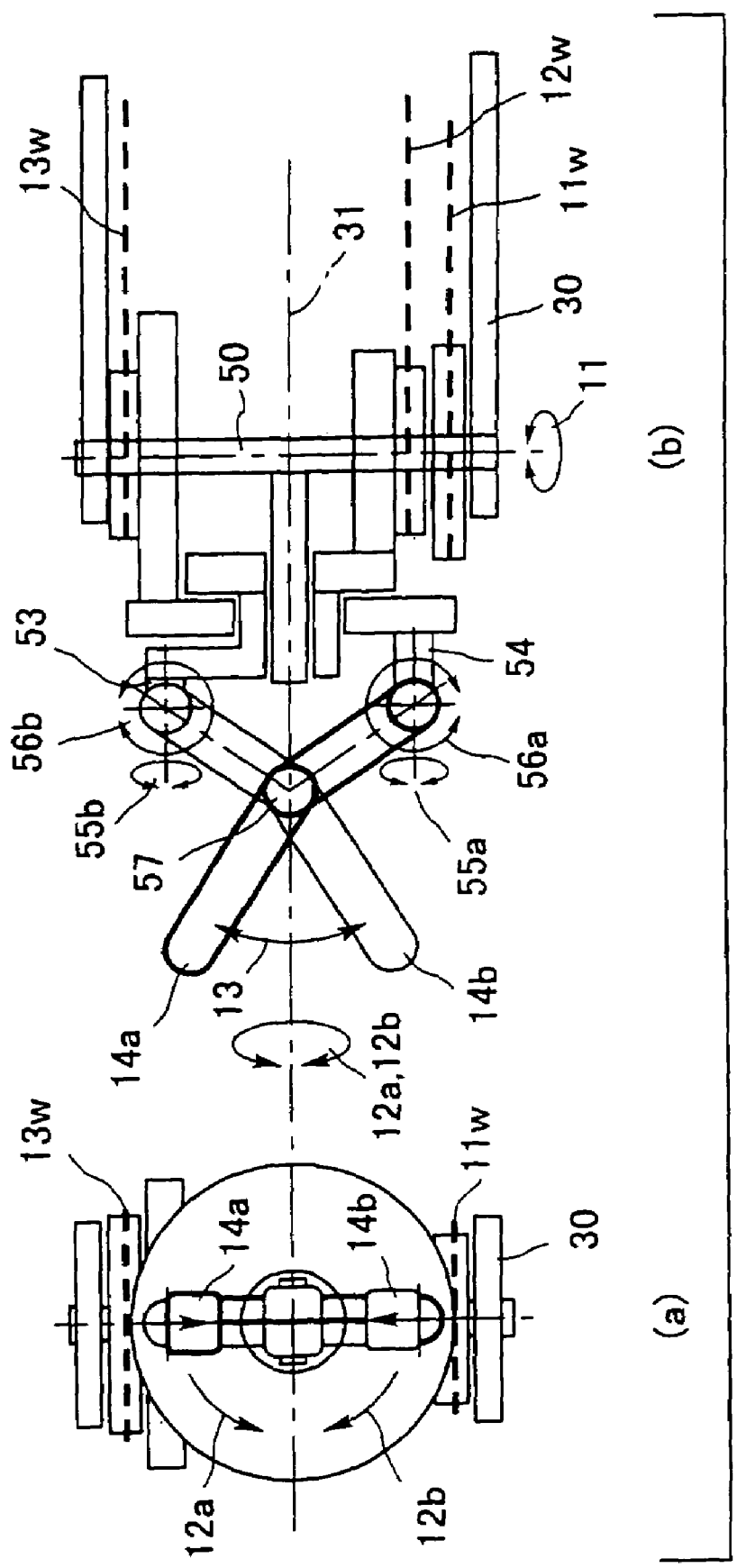
FIGS. 13(a) and 13(b) are a front elevation and a side elevation, respectively, of a working unit that may be employed in the medical manipulator shown in FIG. 1 in a releasing state.
Figure 14:
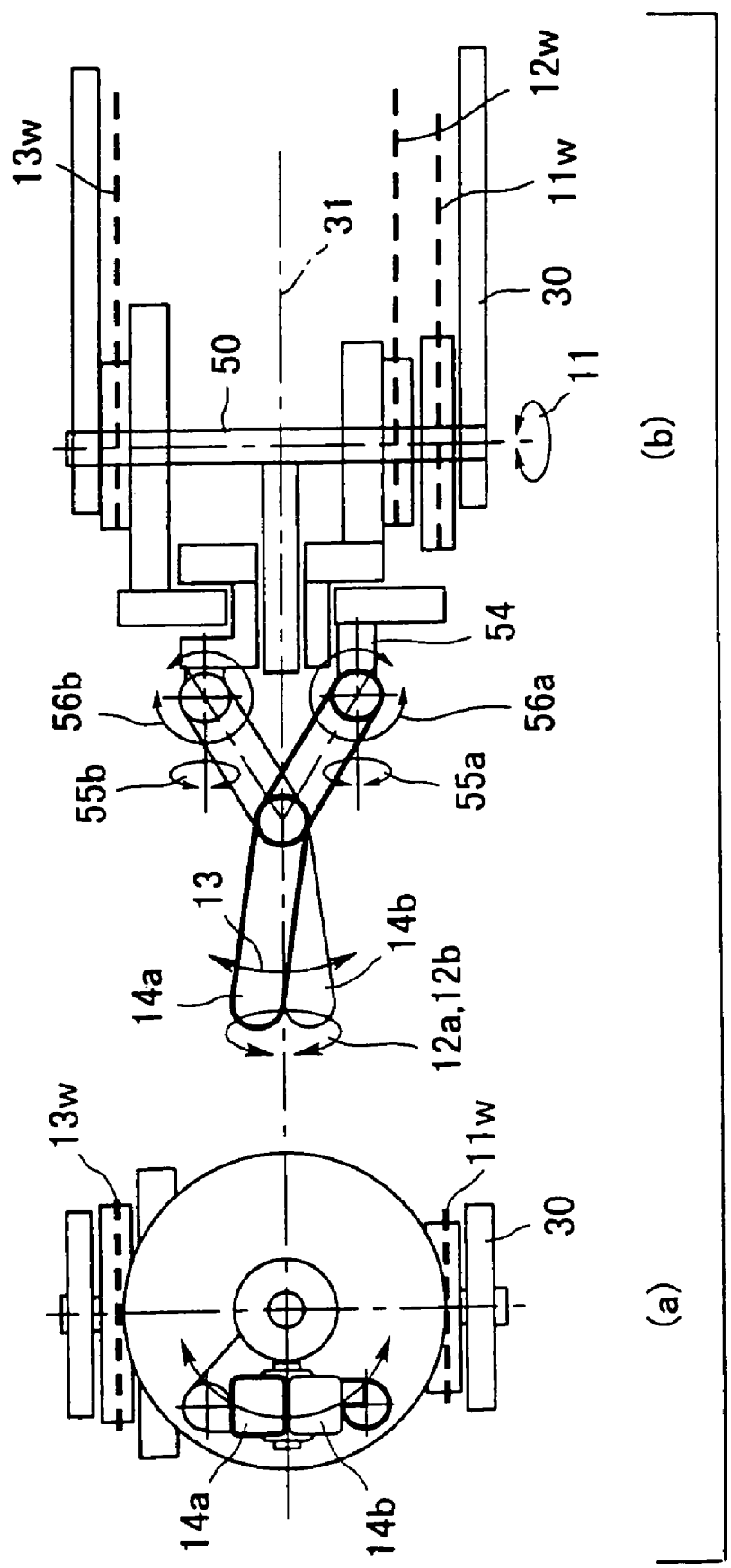
FIGS. 14(a) and 14(b) are a front elevation and a side elevation, respectively, of the working unit shown in FIG. 13 in a gripping state.

The working unit 10 shown in FIGS. 13 and 14 will be described. Middle parts of a pair of gripping bars 14a and 14b are pivotally joined together by a pivot 57. Lower end parts of the gripping bars 14a and 14b are connected to shafts 12a and 12b so as to be turnable about axes 55a and 55b parallel to the axes of the shafts 12a and 12b and about axes 56a and 56b perpendicular to the axes 55a and 55b, respectively. Driving devices 12m and 13m, respectively, drives the gripping bars. The shafts 12a and 12b are turned in the same direction to turn the second joint 12 for the rolling motion of a gripper 14. The shafts 12a and 12b are turned in opposite directions, respectively, to drive the gripper 14 for gripping/releasing actions. The movement of the lower ends of the gripping bars 14a and 14b can be multiplied by increasing the length of front parts of the gripping bars 14a and 14b extending forward beyond the middle parts pivotally joined together by the pivot 57.

Figure 15:
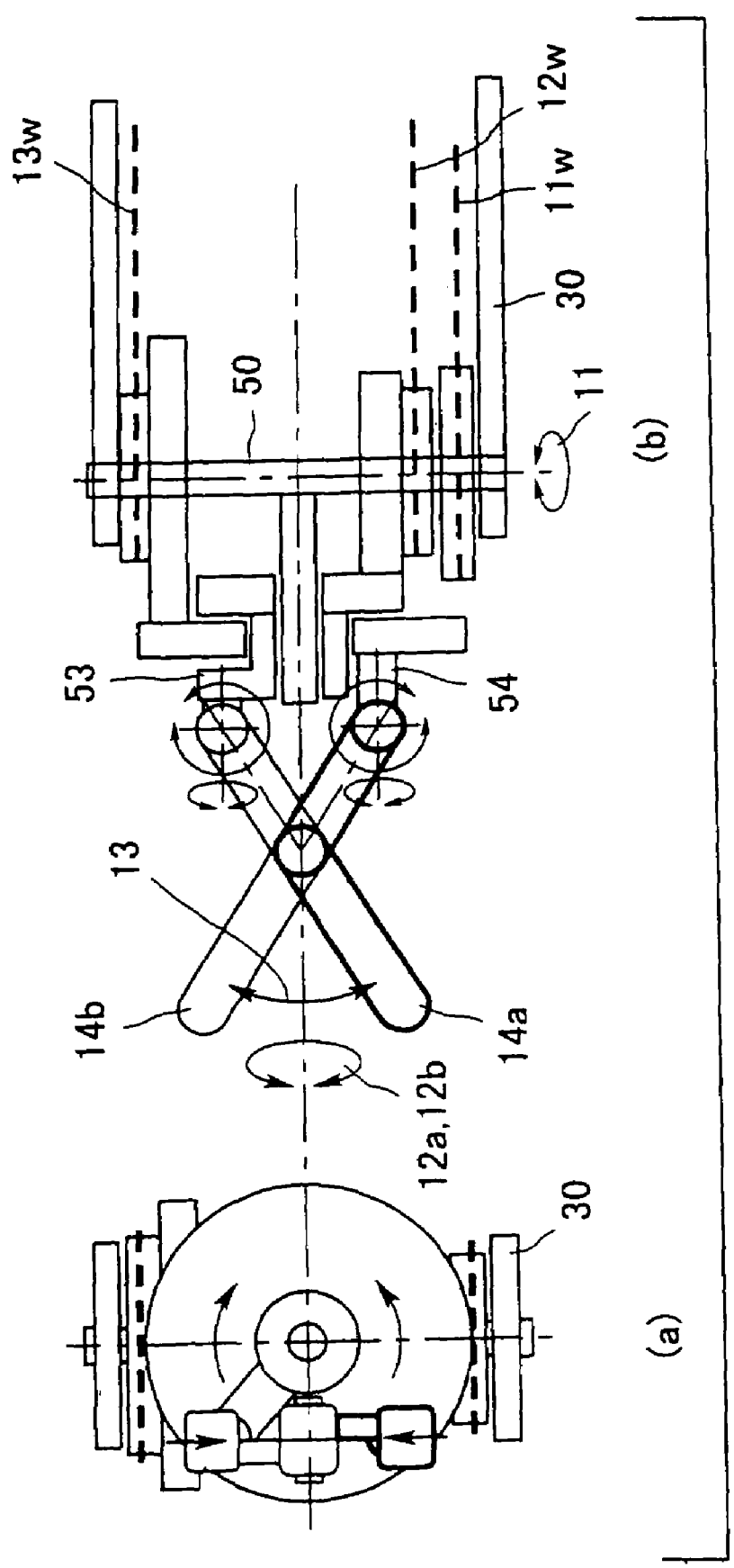
FIGS. 15(a) and 15(b) are a front elevation and a side elevation, respectively, of a working unit that may be employed in the medical manipulator shown in FIG. 1 in a releasing state.
Figure 16:
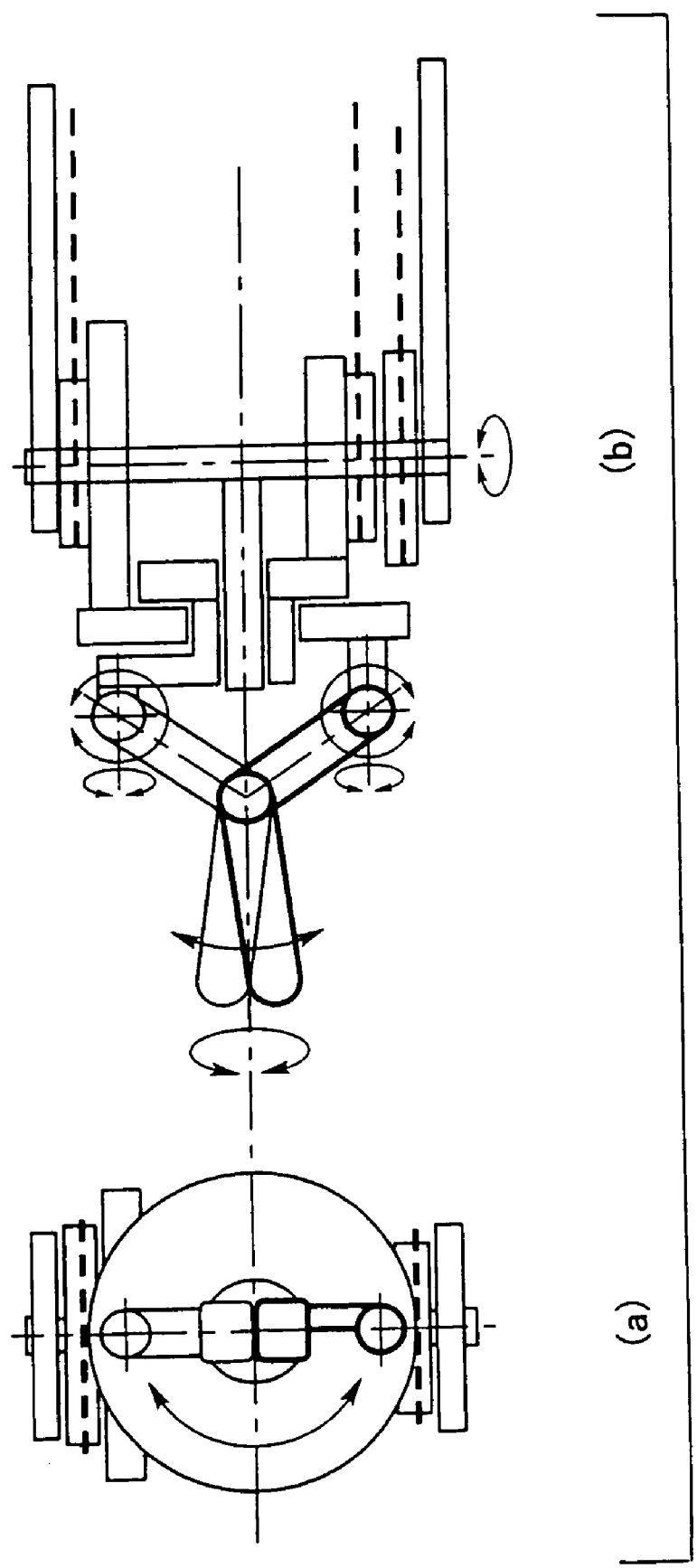
FIGS. 16(a) and 16(b) are a front elevation and a side elevation, respectively, of the working unit shown in FIG. 15 in a gripping state.

The working unit 10 shown in FIGS. 15 and 16 will be described. Turning directions of front parts of gripping bars 14a and 14b of a gripper 14, extending forward from middle parts of the same pivotally joined together of the working unit 10 shown in FIGS. 15 and 16 relative to those of back parts of the gripping bars 14a and 14b extending backward from the middle parts of the same are opposite to those of the front parts of the gripping bars 14a and 14b of the working unit 10 shown in FIGS. 13 and 14. The gripper 14 opens when connecting members 53 and 54 approaches each other, and closes when the connecting members 53 and 54 move away from each other. Since the gripping bars 14a and 14b are linked to form a toggle mechanism, the gripper 14 is able to exert a very large gripping force when the difference in angular position between the connecting members 53 and 54 is around 180°. Such a very large gripping force is available because a direction in which the gripper 14 is opened is nearly perpendicular to a direction in which the lower ends of the gripping bars 14a and 14b are moved, and a force to open the gripper 14 is born by a structure instead of by a driving direction. This working unit 10 is suitable for firmly gripping a fine suture needle.

Figure 17:
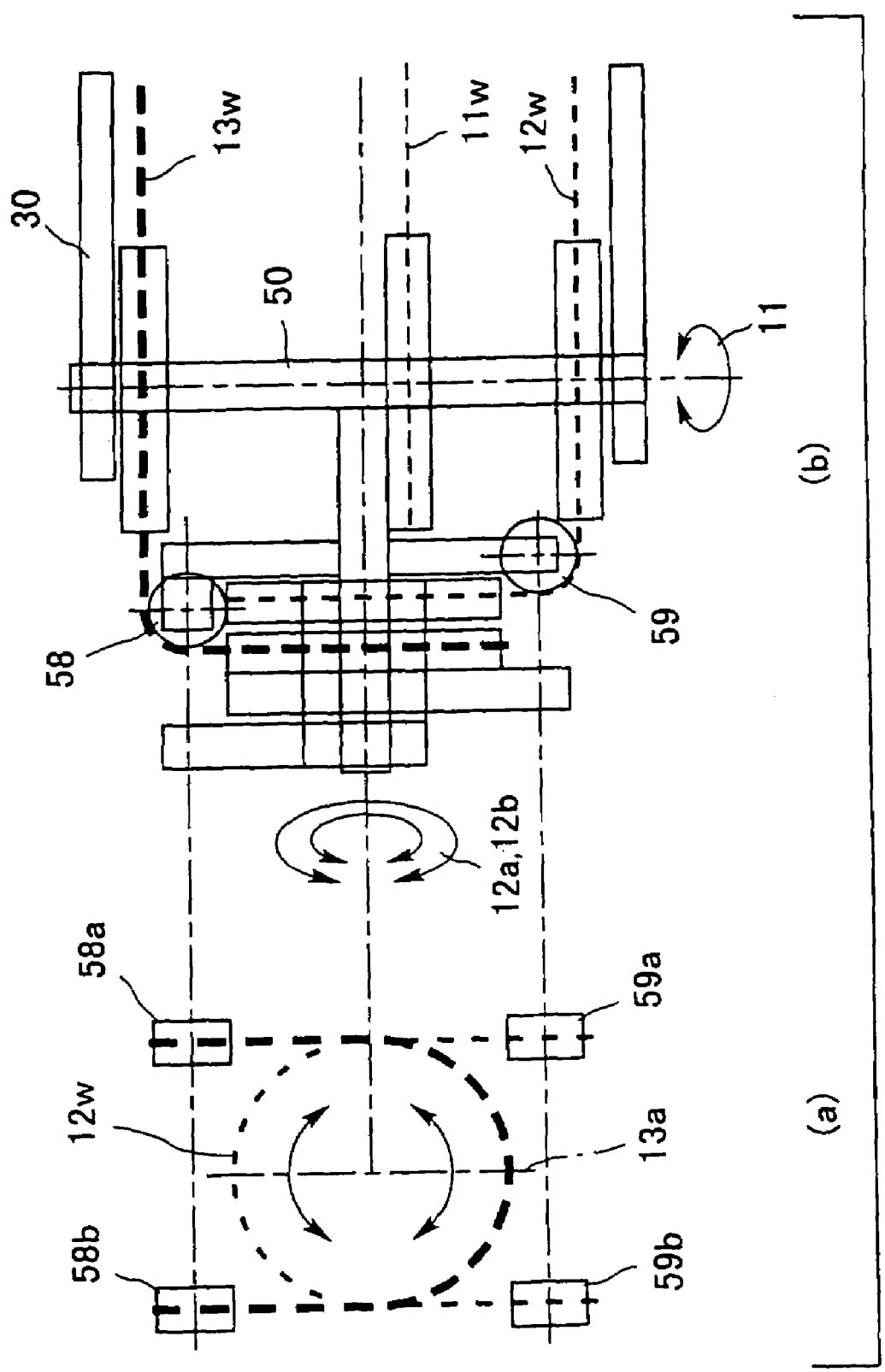
FIGS. 17(a) and 17(b) are a front elevation and a side elevation, respectively, of the working unit of assistance in explaining a power transmitting method.
Figure 18:
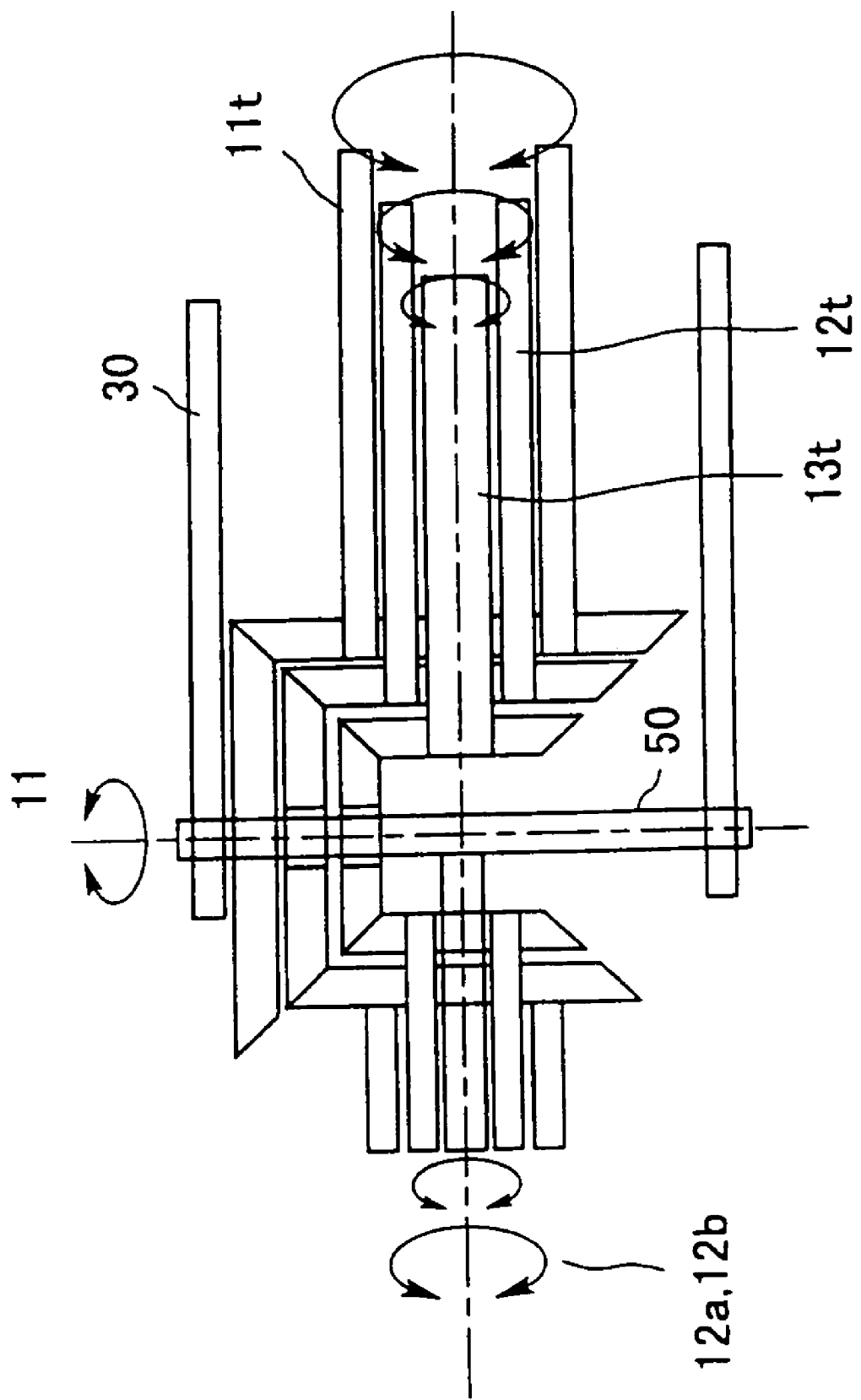
FIG. 18 is a side elevation of the working unit of assistance in explaining a power transmitting method.

The working units 10 shown in FIGS. 11 to 16 uses the wires, the pulleys and the bevel gears (or face gears) to rotate the shafts 12a and 12b on the shaft 12. FIGS. 17 and 18 show other methods.

A method illustrated in FIG. 17 uses only wires and pulleys. The first joint 11, and the shafts 12a and 12b are driven through wires 11w, 12w and 13w, respectively. Pulleys 58 and 59 guide the wires 12w and 13w along curved paths, respectively. The number of turns of the wire on the pulley is dependent on angle for driving. A method illustrated in FIG. 18 uses torque tubes 11t, 12t and 13t. The first joint and the shafts 12a and 12b are driven by the torque tubes 11t, 12t and 13t, respectively.

The shapes of the structural members, the shafts and the connecting members shown in FIGS. 11 to 18 and methods of supporting those components are not limited to those shown in FIGS. 11 to 18 and may be any shapes or any methods provided that the shapes and the methods do not affect adversely to the function of the medical manipulator. For example, the shafts may be fixed and frame may be turned, or the shafts may be turned and the frame may be fixed.

Figure 19:
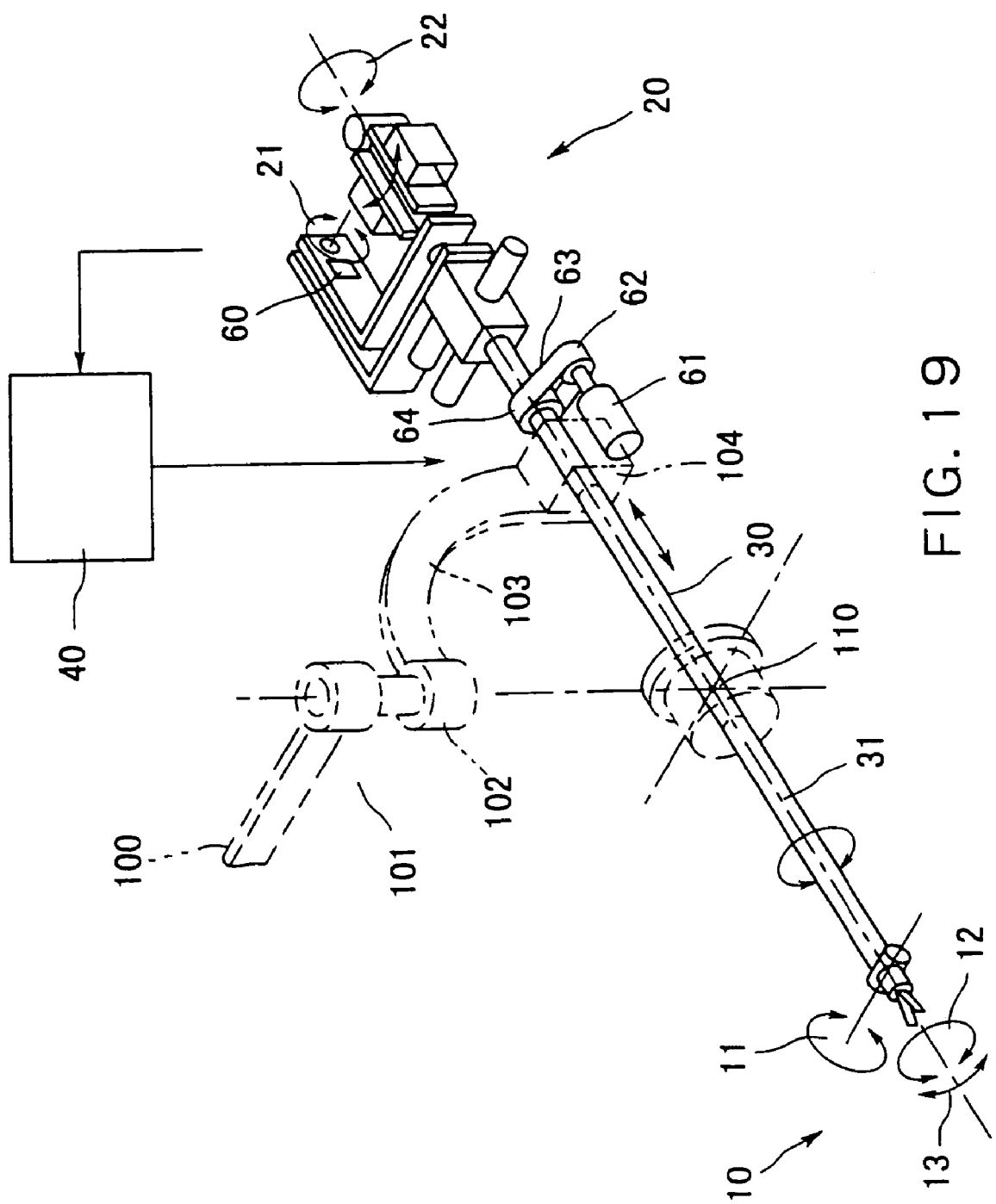
FIG. 19 is a schematic perspective view of a medical manipulator in a second embodiment according to the present invention.

FIG. 19 is a schematic perspective view of a medical manipulator in a second embodiment according to the present invention and FIG. 20 is a skeleton drawing of assistance in explaining the operation of the medical manipulator in the second embodiment.

In the medical manipulator 1 in the first embodiment, it is difficult to change the attitude of the gripper 14 in a direction parallel to an axis perpendicular to the axes of the third joint 21 and the fourth joint 22 when the attitude adjusting unit 23 is in a state for setting the gripper 14 in an attitude nearly equal to a singular attitude where center axis 31 of the connecting unit 30 is aligned with or parallel to the axis of the fourth joint 22 like a state shown in FIG. 19. The medical manipulator in the second embodiment is designed to improve the operability of the same when the gripper is set in an attitude nearly equal to a singular attitude.

The basic configuration of the medical manipulator in the second embodiment is the same as that of the medical manipulator in the first embodiment. In the second embodiment, an operation command unit 20 is provided with a sensor 60, such as a strain gage, capable of sensing a force acting in a direction perpendicular to the axes of a third joint 21 and a fourth joint 22. The sensor 60 is attached to a part of the inner surface of a frame as shown in FIG. 19 to measure bending stress acting in a direction perpendicular to the axes of the third joint 21 and the fourth joint 22.

A driving device (actuator) 61 is mounted on a connecting member 104. The driving device 61 is able to drive a connecting unit 30 through a belt-and-pulley transmission mechanism including a belt 63 and pulleys 62 and 64. A gear transmission mechanism maybe used without any restriction instead of the belt-and-pulley transmission mechanism. A controller 40 controls the driving device 61 on the basis of measured data provided by the sensor 60.

When the medical manipulator is in a state shown in FIG. 20 and an operator operates the end effector control unit to turn the axis of the third joint 21 in a positive direction 120, the driving device 61 is controlled so as to apply a positive torque to the connecting unit 30 to urge the connecting unit 30 to turn in a positive direction 121. If the end effector control unit is operated to turn the axis of the third joint 21 in a negative direction opposite the positive direction 120, the sensor 60 detects a negative bending stress. In this state, the driving device 61 is controlled to apply a negative torque to the connecting unit 30 to urge the connecting unit 30 to turn in a negative direction opposite the positive direction 121.

When the medical manipulator is in a state shown in FIG. 21 with the axis of the third joint 21 extended in a negative direction and an operator operates the end effector control unit to turn the axis of the third joint 21 in a positive direction 122, the sensor 60 detects a positive bending stress and the driving device 61 is controlled so as to apply a negative torque to the connecting unit 30 to urge the connecting unit 30 to turn in a negative direction 123. If the end effector control unit is operated to turn the axis of the third joint 21 in a negative direction opposite the positive direction 122, the sensor 60 detects a negative bending stress. In this state, the driving device 61 is controlled to apply a positive torque to the connecting unit 30 to urge the connecting unit 30 to turn in a positive direction opposite the negative direction 123.

As shown in FIG. 22, a direction in which the driving device 61 turns the connecting unit 30 is determined on the basis of the direction of the bending stress and the direction of the axis of the third joint 21 of the attitude adjusting unit 23. If the third joint 21 is in a neutral attitude (singular attitude), the connecting unit 30 may be turned in either of the opposite directions. In such a case, the connecting unit 30 is tuned in a predetermined direction or may be turned in a direction in which the connecting unit 30 has been recently turned to turn the connecting unit 30 continuously.

The nearer the attitude of the third joint 21 to the singular attitude, the greater is the bending stress. Since the rotating speed must be high, the torque may be varied in proportion to the bending stress. The relation between the bending stress and the torque may be determined properly so that the operability of the medical manipulator is satisfactory. When the attitude of the third joint 21 is far different from the singular attitude, the bending stress is small and, consequently, the torque decreases automatically, which is desirable in respect of safety. The torque may be exerted on the connecting unit 30 only when the direction of the axis of the third joint 21 is in a predetermined angular range around a neutral direction, such as in an angular range of ±10° with respect to the neutral direction.

If a torque is applied to the connecting unit 30 when the direction of the axis of the third joint 21 is in the angular range of ±10°, the working unit 20 does not move suddenly because the working unit 10 and the operation command unit 20 are the same in structural configuration and the degree of freedom of motion, and the attitude of the working unit 10 is analogous with an attitude of the operation command unit 20 set by the operator.

The driving device 61 may be used as an actuator for compensating a torque about the center axis 31 of the connecting unit 30 produced by the weight of the medical manipulator. The torque about the center axis 31 produced by the weight of the medical manipulator can be easily calculated with reference to the attitudes of the shafts of the medical manipulator and the torque can be easily compensated.

Figure 23:
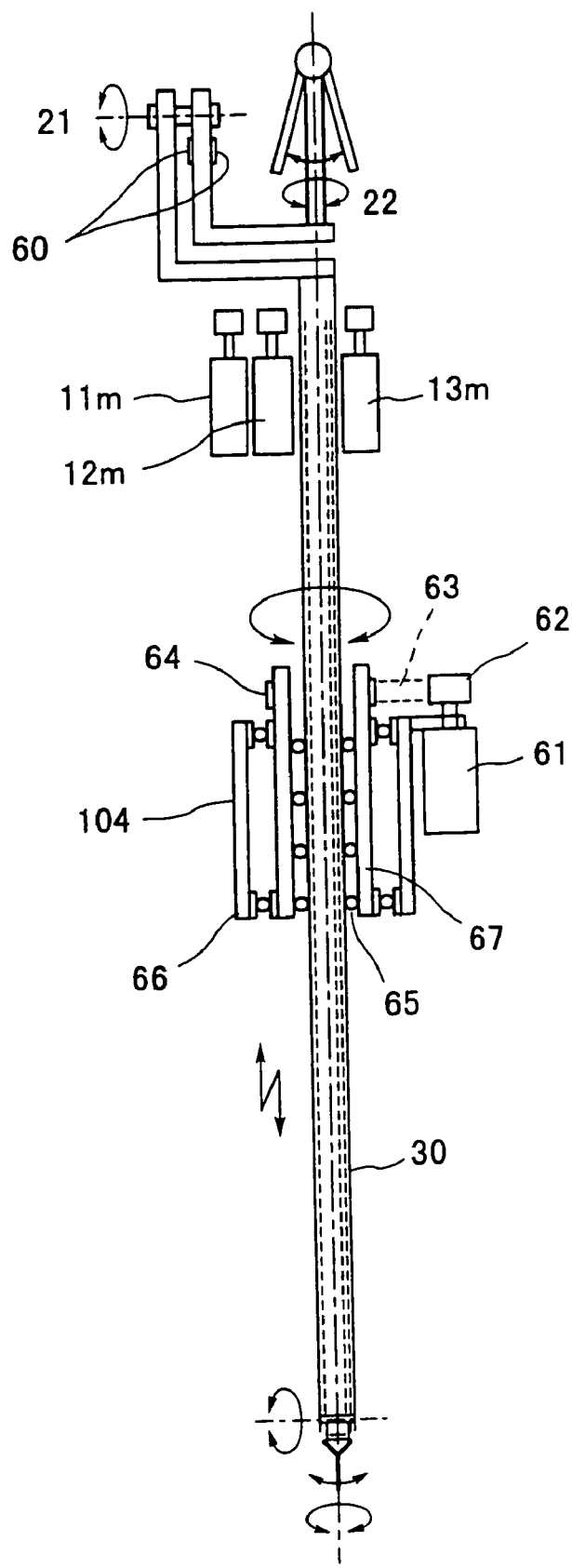
FIG. 23 is a side elevation of the medical manipulator shown in FIG. 19.
Figure 24:
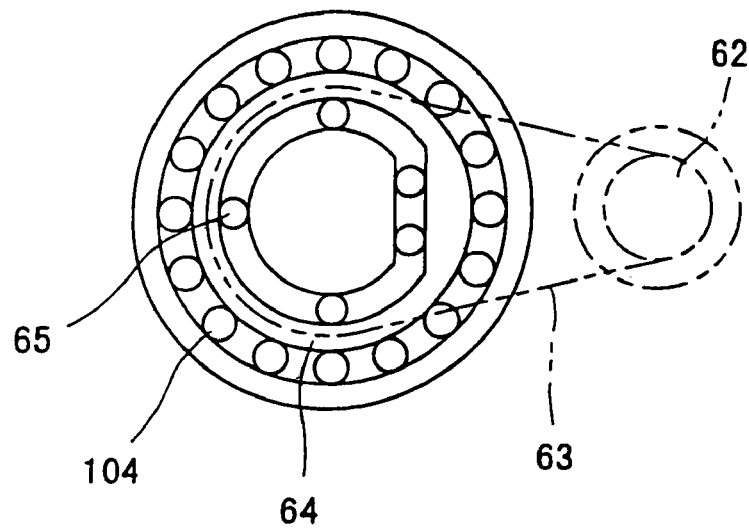
FIG. 24 is a sectional view of a supporting and connecting part shown in FIG. 23.
Figure 25:
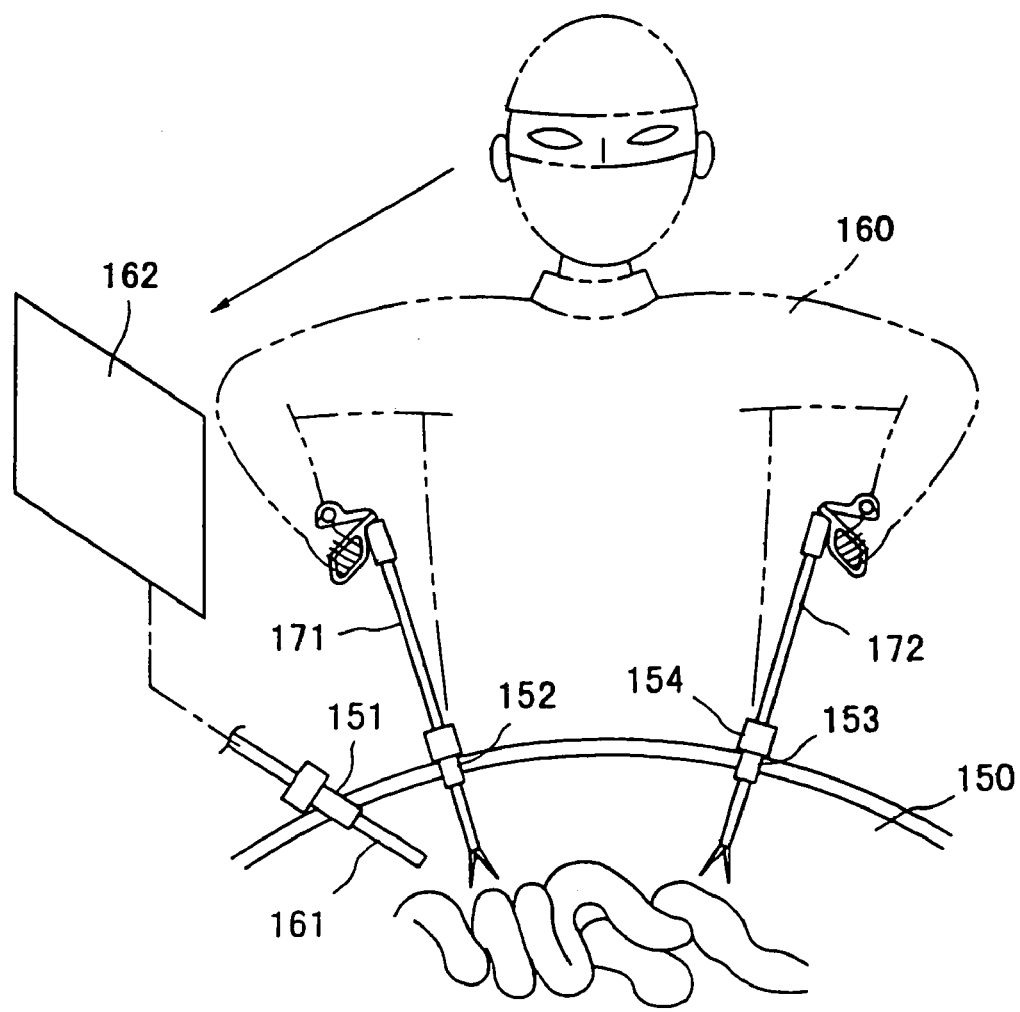
FIG. 25 is a pictorial view of assistance in explaining a conventional medical manipulator, i.e., forcepts.
Figure 26:
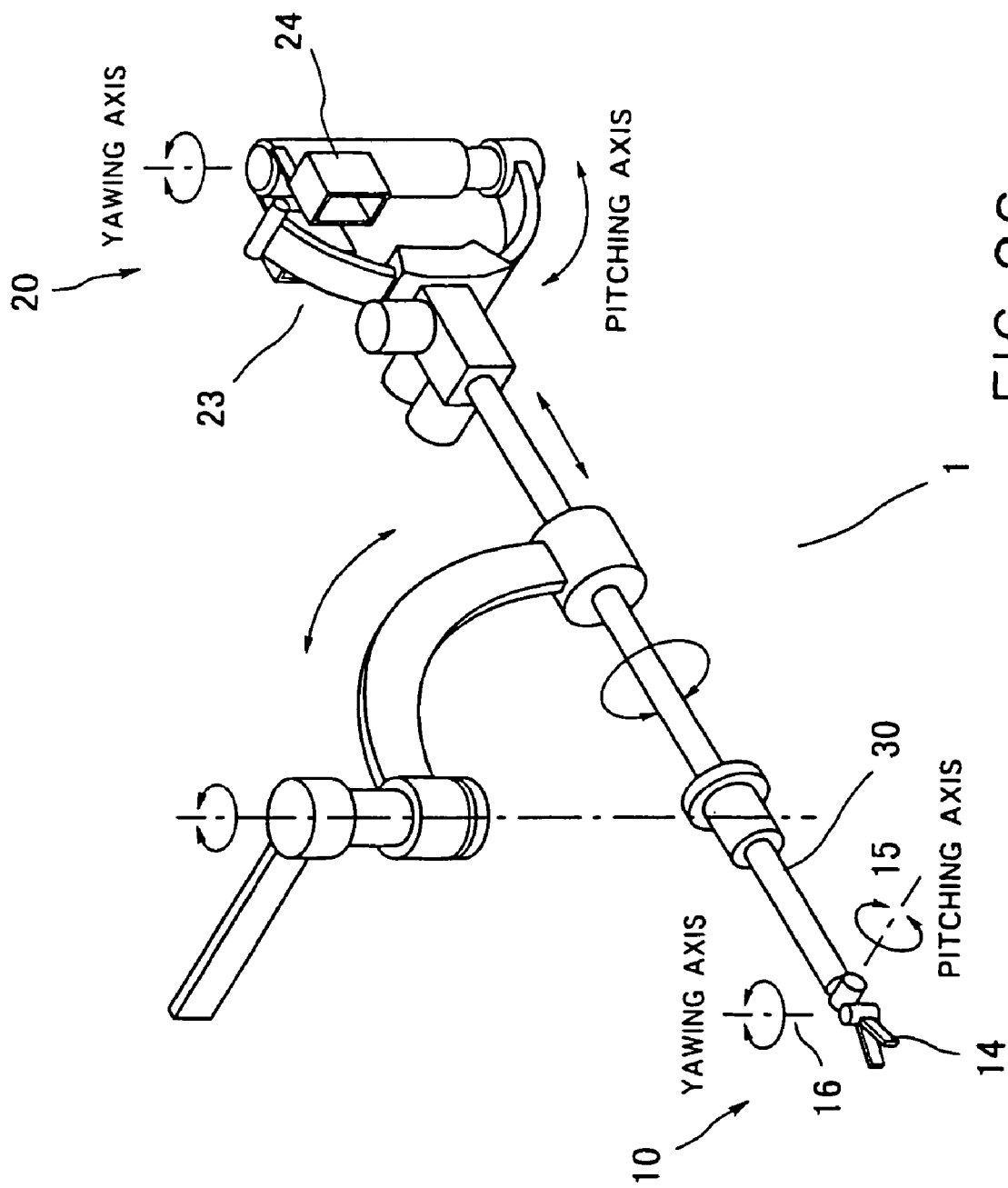
FIG. 26 is a schematic perspective view of a known medical manipulator.

FIG. 23 is a view of assistance in explaining a method of applying a torque about the center axis 31 of the connecting unit 30 to the connecting unit 30. The medical manipulator 1 is supported on the connecting member 104 so as to be turnable about the center axis 31 of the connecting unit 30 and to be linearly movable in parallel to the center axis 31 of the connecting unit 30. As shown in FIG. 23, the connecting unit 30 is supported in a linear-motion bearing 65 and a rotary bearing 66. The connecting unit 30 has a D-shaped cross section. The driving device 61 turns the sleeve 67 of the linear-motion bearing 65 through the belt-and-pulley transmission mechanism including the belt 63 and the pulleys 62 and 64. Thus, the connecting unit 30 is supported on the connecting member 104 for linear movement and rotation, and torque can be applied to the connecting unit 30.

Figure 29:
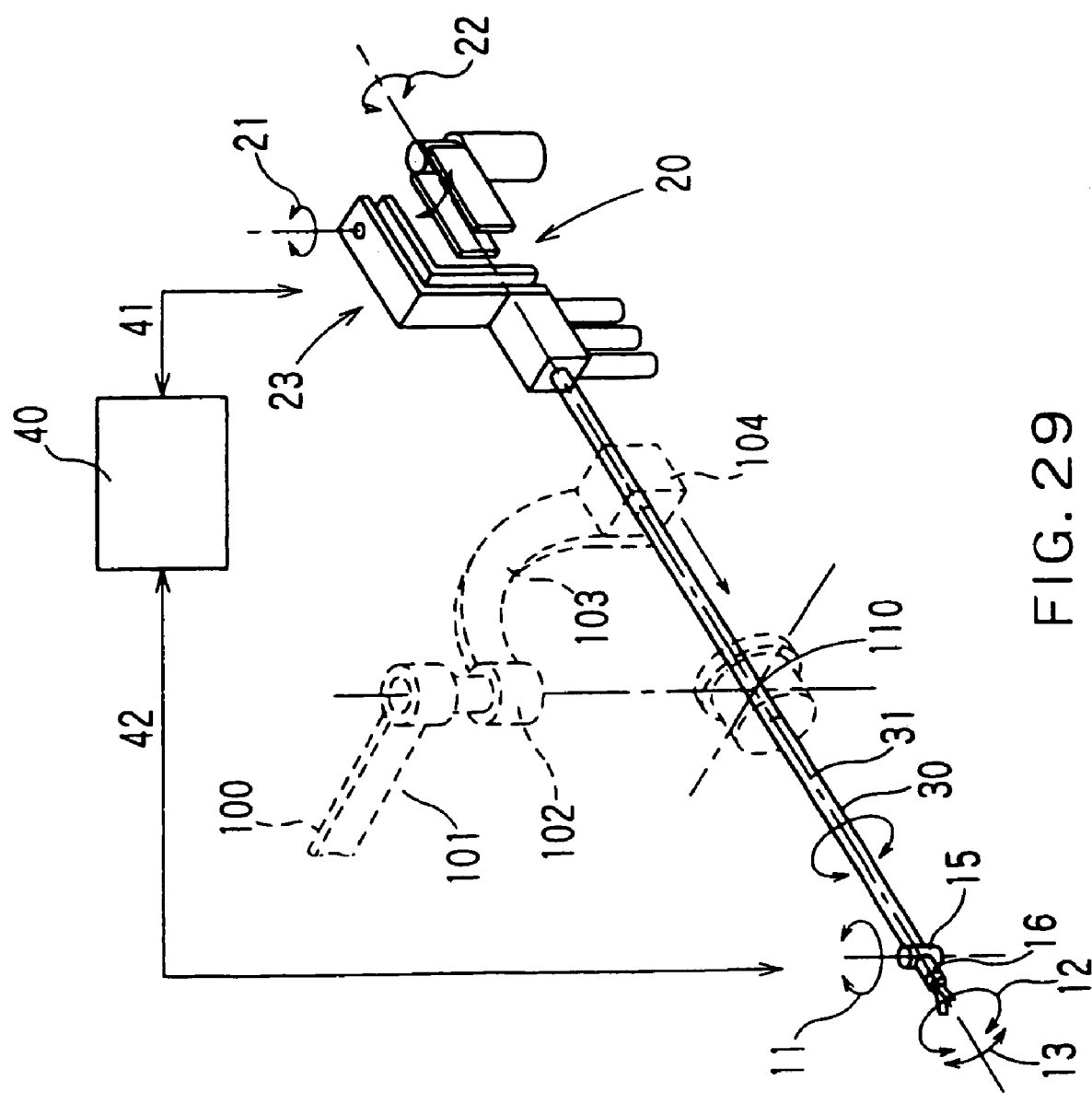
FIG. 29 is a schematic perspective view of a manipulator having a first or a third joint serving as a yawing shaft.

In the first and the second embodiment, the first joint 11 or the third joint 21 is a pitching shaft. However, the first joint 11 or the third joint 21 does not need necessarily to be a pitching shaft and may be a yawing shaft as shown in FIG. 29.

As apparent from the foregoing description, according to the present invention, since the support unit is able to change the attitude of the end effector in two or more degrees of freedom of motion, the operation command unit and the working unit are connected mechanically by the connecting unit, and the operator's actions, such as actions for manipulating a curved suture needle for suturing, and the actions of the manipulator are identical, the operation command unit can be smoothly moved in a direction desired by the operator. Thus, the manipulator is excellent in operability. Since operating force exerted by the operator is assisted by power when the end effector is set in a singular attitude or an attitude similar to the particular attitude, the operability of the end effector in particular directions does not becomes quite unsatisfactory and the end effector is able to exert a sufficiently high gripping force.

Although the invention has been described in its preferred embodiments with a certain degree of particularity, obviously many changes and variations may be made therein. It is therefore to be understood that the present invention may be practiced otherwise than as specifically described herein without departing from the scope and spirit thereof.

What is claimed is:

1. A manipulator comprising:
   an operation command unit including an attitude adjusting unit and an end effector control unit;
   a connecting unit having one end connected to the operation command unit;
   a working unit connected to the other end of the connecting unit and including an end effector and a support unit supporting the end effector for motions in at least two degrees of freedom of motion; and
   a control unit configured to transmit an operation command provided by the attitude adjusting unit to the support unit to adjust the attitude of the end effector and configured to transmit an operation command provided by the end effector control unit to the end effector to operate the end effector;
   wherein the support unit includes a first joint configured to turn about a first axis perpendicular to a center axis of the connecting unit, and a second joint configured to turn about a second axis perpendicular to the first axis, and
   the end effector includes a center axis substantially parallel to the second axis.

2. The manipulator according to claim 1, wherein the center axis, the first axis and the second axis intersect each other at a single point.

3. A manipulator comprising:
   an operation command unit including an attitude adjusting unit and an end effector control unit;
   a connecting unit having one end connected to the operation command unit;
   a working unit connected to the other end of the connecting unit and including an end effector and a support unit configured to support the end effector for motions in at least two degrees of freedom of motion; and
   a control unit configured to transmit an operation command provided by the attitude adjusting unit to the support unit to adjust the attitude of the end effector and configured to transmit an operation command provided by the end effector control unit to the end effector to operate the end effector;
   wherein the support unit includes a first joint configured to turn about a first axis perpendicular to a center axis of the connecting unit, and a second joint configured to turn about a second axis perpendicular to the first axis, and the end effector control unit includes a handle part configured to be gripped by fingers and a longitudinal direction is substantially in parallel to the first axis.

4. The manipulator according to claim 3, wherein the end effector includes a center axis, and the center axis, the first axis and the second axis intersect each other at a single point.

5. A manipulator comprising:

an operation command unit including an attitude adjusting unit and an end effector control unit;

a connecting unit having one end connected to the operation command unit;

a working unit connected to the other end of the connecting unit and including an end effector and a support unit configured to support the end effector for motions in at least two degrees of freedom of motion; and a control unit configured to transmit an operation command provided by the attitude adjusting unit to the support unit to adjust the attitude of the end effector and configured to transmit an operation command provided by the end effector control unit to the end effector to operate the end effector; and a driving unit including a first driving device, a second driving device and a third driving device and the first driving device, the second driving device and the third driving device have a longitudinal outside shape, and an axis of the longitudinal outside shape is parallel each other between the first driving device, the second driving device and the third driving device;

wherein the support unit includes a first joint configured to turn about a first axis perpendicular to a center axis of the connecting unit, and a second joint configured to turn about a second axis perpendicular to the first axis, and the driving unit is configured to drive the first joint and the second joint, and is configured to turn and drive the end effector.

6. The manipulator according to claim 5, wherein the end effector includes a center axis, and the center axis, the first axis and the second axis intersect each other at a single point.

7. The manipulator according to claim 5, wherein the driving unit is disposed between the operation command unit and the connecting unit.

* * * * *